United States Patent [19]

Henning et al.

[11] Patent Number: 4,624,962
[45] Date of Patent: Nov. 25, 1986

[54] SUBSTITUTED DERIVATIVES OF 2-AZABICYCLO-[3.3.0]OCTANES

[75] Inventors: Rainer Henning, Frankfurt am Main; Hansjörg Urbach, Kronberg; Rolf Geiger, Frankfurt am Main; Volker Teetz, Hofheim am Taunus; Bernward Schölkens, Kelkheim, all of Fed. Rep. of Germany

[73] Assignee: Hoechst Aktiengesellschaft, Frankfurt am Main, Fed. Rep. of Germany

[21] Appl. No.: 697,340

[22] Filed: Feb. 1, 1985

Related U.S. Application Data

[62] Division of Ser. No. 413,663, Sep. 1, 1982, Pat. No. 4,515,803.

[30] Foreign Application Priority Data

Sep. 3, 1981 [DE] Fed. Rep. of Germany ....... 3134933

[51] Int. Cl.[4] .................... A61K 31/40; C07D 209/52
[52] U.S. Cl. .................................... 514/412; 546/226;
546/245; 514/338; 546/273; 546/332; 514/339;
548/146; 548/181; 514/344; 548/183; 548/184;
514/348; 548/187; 548/189; 514/349; 548/194;
548/204; 514/365; 548/273; 548/300; 514/397;
548/336; 548/358; 514/399; 548/374; 548/378;
514/406; 548/451; 548/452; 514/407; 548/454;
548/455; 514/419; 548/465; 548/467; 514/44;
548/492; 548/495; 514/447; 548/517; 549/58;
540/597; 549/76; 560/34; 540/607; 560/130;
560/169; 562/439; 562/560; 544/145; 544/148;
546/114; 546/118; 546/146; 546/147; 546/156;
546/189; 546/200; 546/202; 546/208; 546/209;
546/212

[58] Field of Search ............... 548/452, 454, 455, 467, 548/336, 358, 374, 146, 183–184, 187, 189, 194; 546/200; 514/412, 339, 365, 397, 406

[56] References Cited

U.S. PATENT DOCUMENTS 4,284,779 8/1981 Ondetti et al. ..................... 546/189

FOREIGN PATENT DOCUMENTS

A11813  10/1978  European Pat. Off. .
A218549  4/1980   European Pat. Off. .
A237231  3/1981   European Pat. Off. .
A149589  9/1981   European Pat. Off. .
A149605  10/1981  European Pat. Off. .
A161684  3/1982   European Pat. Off. .
A161745  3/1982   European Pat. Off. .
2624094  5/1976   Fed. Rep. of Germany .
2907601  2/1979   Fed. Rep. of Germany .
2914059  4/1979   Fed. Rep. of Germany .
135387   5/1979   Fed. Rep. of Germany .

OTHER PUBLICATIONS

Henning, et al., "Chemical Abstracts", vol. 99, 1983, col. 99:88067e.

Primary Examiner—Richard L. Raymond
Assistant Examiner—James H. Turnipseed
Attorney, Agent, or Firm—Curtis, Morris & Safford

[57] ABSTRACT

Compounds of the formula I

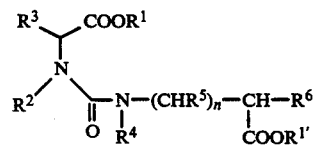

in which
n denotes 0–3,
$R^1$ and $R^{1'}$ are the same or different and denote hydrogen, alkyl or alkenyl, phenyl or benzyl, each substituted as desired;
$R^2$ denotes hydrogen, alkyl or alkenyl;
$R^3$ denotes hydrogen, alkyl, hydroxyalkyl, alkoxyalkyl or aminoalkyl, alkanoylaminoalkyl, guanidinoalkyl, imidazolylalkyl, indolylalkyl, mercaptoalkyl or alkylthioalkyl, phenylalkyl, hydroxphenylalkyl, phenoxyalkyl or phenylthioalkyl, or $R^2$ and $R^3$, together with the C and N atoms carrying them, denote a saturated or unsaturated 4- to 8-membered monocyclic or 8- to 10-membered bicyclic isocycle or heterocycle, optionally monosubstituted or disubstituted by hydroxyl, alkoxy having 1 to 3 C atoms or alkyl,
$R^4$ denotes hydrogen, alkyl, alkenyl, alkadienyl, alkinyl, alkeninyl or alkadiinyl, cycloalkyl, phenyl, benzyl, phenethyl or phenylpropyl, each of which can be optionally monosubstituted or disubstituted;
$R^5$ denotes hydrogen or alkyl, hydroxyl or alkoxy and
$R^6$ denotes hydrogen, optionally substituted alkyl, cycloalkyl, alkenyl, optionally monosubstituted or disubstituted phenyl or naphthyl, their salts, a process for their preparation and their use as medicaments.

13 Claims, No Drawings

SUBSTITUTED DERIVATIVES OF 2-AZABICYCLO-[3.3.0]OCTANES

This application is a division of application Ser. No. 413,663, filed Sept. 1, 1982 now U.S. Pat. No. 4,515,803. The invention relates to compounds of the formula (I)

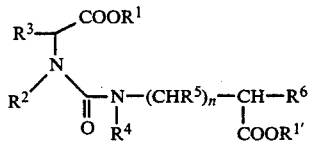

in which: n denotes a whole number between 0 and 3 inclusive, $R^1$ and $R^{1'}$, being the same or different, denote hydrogen; alkyl or alkenyl having 1–8 C atoms; phenyl or benzyl, each substituted if desired by methyl, halogen, methoxy or nitro; $R^2$ denotes hydrogen, alkyl or alkenyl having 1–8 C atoms; $R^3$ denotes hydrogen; alkyl having 1–10 C atoms; hydroxyalkyl, alkoxyalkyl or aminoalkyl each having 1–5 C atoms; alkanoylaminoalkyl having 1–7 C atoms; guanidinoalkyl, imidazolylalkyl, indolylalkyl, mercaptoalkyl or alkylthioalkyl each having 1–6 alkyl C atoms; phenylalkyl having 1–5 alkyl C atoms; hydroxyphenylalkyl having 1–5 alkyl C atoms; phenoxyalkyl or phenylthioalkyl each having 1–4 alkyl C atoms, or $R^2$ and $R^3$ together with the C and N atoms carrying them form a saturated or unsaturated 4–8-membered monocyclic or 8–10-membered bicyclic ring system, which contains 1–2 oxygen, 1–2 sulfur and/or 1–4 nitrogen atoms and can be monosubstituted or disubstituted by hydroxyl, alkoxy having 1–3 C atoms, alkyl having 1–3 C atoms or phenyl; $R^4$ denotes hydrogen, alkyl, alkenyl, alkadienyl, alkinyl, alkeninyl or alkadiinyl having 1–8 C atoms, cycloalkyl having 3–6 C atoms; phenyl, benzyl, phenethyl or phenylpropyl, each of which can be monosubstituted or disubstituted by halogen, hydroxyl, acetoxy, carboxy, carboxamido, sulfonamido, nitro, methyl, ethyl, methoxy, ethoxy or methylenedioxy; $R^5$ denotes hydrogen or alkyl having 1–5 C atoms, hydroxyl or alkoxy having 1–3 C atoms; $R^6$ denotes hydrogen; alkyl having 1–12 C atoms; cycloalkyl having 3–12 C atoms; alkenyl having 1–12 C atoms; phenyl or naphthyl, each of which can be monosubstituted or disubstituted by halogen, hydroxyl, acetoxy, carboxy, carboxamido, sulfonamido, nitro, methyl, ethyl, methoxy, ethoxy or methylenedioxy; or alkyl having 1–6 C atoms, which is substituted by halogen, hydroxyl, alkoxy having 1–3 C atoms, phenoxy, amino, dialkylamino having 1–6 C atoms, alkanoylamino having 1–3 C atoms, mercapto, alkylthio having 1–3 C atoms, phenylthio, phenylsulfinyl, phenylsulfonyl, phenyl, biphenylyl, naphthyl or heteroaryl, it being possible for the phenyl or naphthyl in turn to be monosubstituted or disubstituted by halogen, methyl, ethyl, methoxy, ethoxy, nitro, amino, alkylamino, dialkylamino, acetylamino, cyano, methylenedioxy or sulfonamido and the heteroaryl to be substituted by the substituents mentioned and additionally by phenyl, and their salts.

Compounds of the formula I are preferred in which the substituents have the following meaning: n is 0 to 2, $R^1$ and $R^{1'}$ are hydrogen, alkyl or alkenyl having 1 to 4 C atoms, or benzyl optionally substituted in the phenyl nucleus by methyl, halogen, methoxy or nitro; $R^2$ is hydrogen, alkyl, alkenyl or alkinyl having 1 to 5 C atoms; $R^3$ is the radical of a natural aminoacid, acetylaminobutyl, methoxymethyl, methoxyethyl, phenoxymethyl, methylthiomethyl, methylthioethyl or phenylthiomethyl; $R^2$ and $R^3$ can be, together with the carbon or nitrogen atom carrying them, part of a saturated or unsaturated 4- to 8-membered monocyclic or 8- to 10-membered bicyclic ring system, which, apart from carbon, can also contain an oxygen, sulfur and/or 1 to 3 nitrogen atoms in each case, and suitable ring systems of this type are: as monocyclic systems, azetidine, dihydropyrrole, pyrrolidine, piperidine, the latter two being optionally monosubstituted or disubstituted by methoxy, ethoxy, methyl, ethyl or phenyl, hexahydroazepine, octahydroazocine, morpholine, N'-alkylpiperazine having 1 to 3 C atoms, N'-phenylpiperazine and thiazolidine, optionally substituted in the 2-position by methyl, ethyl, phenyl, hydroxyphenyl or methoxyphenyl, and as bicyclic systems, tetrahydroquinoline, tetrahydroisoquinoline, decahydroquinoline, decahydroisoquinoline, dihydroindole, octahydroindole, 2-azabicyclo[3.3.0]octane, all of which being optionally monosubstituted or disubstituted by methyl or methoxy, tetrahydroimidazolo[2,3-c]pyridine, tetrahydrothieno[2,3-c]pyridine, tetrahydrothieno[3,2-c]pyridine and tetrahydrothieno[3,4-c]pyridine; $R^4$ is hydrogen; straight-chain or branched alkyl, alkenyl or alkinyl having 1 to 5 C atoms; cycloalkyl, such as cyclopropyl, cyclobutyl, cyclopentyl, cyclohexyl; phenyl; benzyl or phenethyl; $R^5$ is hydrogen, methyl, ethyl, hydroxyl, methoxy or benzyl; $R^6$ is hydrogen, alkyl having 1 to 8 carbon atoms or phenyl which can be monosubstituted or disubstituted by methyl, halogen, methoxy, acetoxy or nitro; substituted alkyl having 1 to 4 C atoms, suitable substituents being: halogen, hydroxyl, methoxy, ethoxy, phenoxy, amino, methylamino, dimethylamino, anilino, acetylamino, benzamido, mercapto, phenylthio, phenylsulfinyl, phenylsulfonyl; phenyl which is optionally monosubstituted or disubstituted by halogen, methyl, ethyl, methoxy, ethoxy, nitro, amino, methylamino, dimethylamino, acetylamino, cyano, methylenedioxy or sulfonamido; biphenylyl, heteroaryl, such as pyridyl, thienyl, indolyl, benzothienyl, imidazolyl, pyrazolyl and thiazolyl, optionally substituted by halogen, methyl, methoxy and phenyl.

Compounds of the formula (I) are particularly preferred in which the substituents have the following meaning: n is 0 or 1, $R^1$ and $R^{1'}$ are hydrogen, methyl, ethyl, n-butyl, t-butyl, benzyl or p-nitrophenyl, $R^2$ is hydrogen, methyl, ethyl or n-butyl, $R^3$ is the radical of a natural aminoacid or acetylaminobutyl, methoxymethyl, methoxyethyl, phenoxymethyl, methylthiomethyl, methylthioethyl or phenylthiomethyl; $R^2$ and $R^3$ can be, together with the carbon or nitrogen atom carrying them, part of a saturated or unsaturated 5- to 7-membered monocyclic or 8- to 10-membered bicyclic ring system which, apart from carbon, can also contan an oxygen or sulfur atom and/or 1 to 2 nitrogen atoms in each case, and suitable ring systems are: as monocyclic systems, dihydropyrrole; pyrrolidine, piperidine, the latter two being optionally substituted by methoxy, methyl, or phenyl, hexahydroazepine, thiazolidine, optionally substituted in the 2-position by methyl, phenyl or hydroxyphenyl, and as bicyclic systems, tetrahydroisoquinoline, decahydroisoquinoline, dihydroindole, octahydroindole, 2-azabicyclo[3.3.0]octane, all optionally monosubstituted or disubstituted by methyl or methoxy, tetrahydroimidazolo[2,3-c]pyridine, tetrahydrothieno[2,3-c]pyridine, tetrahydrothieno[3,2-c]pyridine and tetrahydrothieno[3,4-c]pyridine, $R^4$ is methyl, ethyl, n-propyl, n-butyl, isopropyl, isobutyl, cyclopropyl, cyclobutyl, allyl, butenyl, propargyl, butinyl or tert.-butyl, $R^5$ is hydrogen, methyl or benzyl, $R^6$ is hydrogen, straight-chain or branched alkyl or alkenyl having 1 to 6 C atoms or cycloalkyl having 3 to 6 C atoms; substituted alkyl having 1 to 3 C atoms, suitable substituents being: methoxy, ethoxy, phenoxy, dimethylamino, anilino, benzamido, phenylthio, phenylsulfinyl, phenylsulfonyl and phenyl optionally monosubstituted or disubstituted by halogen, methyl, methoxy, nitro, amino, methylamino, dimethylamino, acetylamino, cyano or methylenedioxy; biphenylyl; heteroaryl, such as pyridyl, thienyl, indolyl, benzothienyl, imidazolyl or thiazolyl, optionally substituted by chlorine, methyl, methoxy or phenyl.

Special attention is drawn to compounds of the formula I in which n is 1, $R^1$ denotes hydrogen, $R^2$ and $R^3$, together with the C and N atoms carrying them, denote the 1,2,3,4-tetrahydroisoquinoline system, the octahydroindole system or the 2-azabicyclo[3.3.0]octane system, $R^4$ denotes ethyl, $R^5$ denotes hydrogen and $R^6$ denotes β-phenylethyl.

The compounds of the formula I contain several asymmetric C atoms and thus they are in the form of enantiomers and diastereomers. The invention comprises the pure isomers and their mixtures. Those compounds are preferred which have the S-configuration at the carbon atom which carries the substituent $R^3$. Those compounds are particularly preferred which have the S-configuration both at the carbon atom carrying the substituent $R^3$ and at that carrying the $COOR^1$ group. In compounds of the formula I, in which $R^2$ and $R^3$, together with the C and N atoms carrying them, represent a saturated bicyclic ring system with carbon atoms as bridgehead atoms, the cis-configuration with an endo-orientation of the $COOR^1$ group relative to the bicyclic ring system is preferred. Particularly preferred bicyclic ring systems are endo-cis-octahydroindole and endo-cis-2-azabicyclo[3.3.0]octane.

The isomers can be prepared pure, for example by crystallization of suitable salts, such as the cyclohexylamine or dicyclohexylamine salts or by chromatography on silica gel or ion exchangers. Where appropriate, the separations are carried out on suitable precursors.

If the compounds of the formula I have acid character, the invention comprises the free acids, their alkali metal and alkaline earth metal salts and also the salts with pharmaceutically acceptable amines, such as cyclohexylamine or dicyclohexylamine and basic aminoacids, such as lysine and arginine.

The invention further relates to a process for the preparation of the compounds of the formula I. The process comprises reacting an aminoacid ester of the formula II

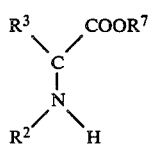
(II)

in which $R^7$ has the same meaning as $R^1$, but is not hydrogen, with phosgene and then with a compound of the formula IV

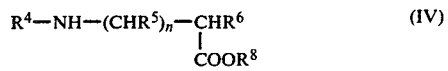

in which $R^8$ has one of the meanings of $R^7$, or reacting a compound of the formula IV with phosgene and then with a compound of the formula II, and, if appropriate, subjecting the products obtained to hydrolysis.

In the process variant first mentioned, a compound of the formula II, in which $R^7$ has the same meaning as $R^1$ in formula I, but is not hydrogen, is reacted with phosgene to give the N-chlorocarbonyl derivative of the formula (III).

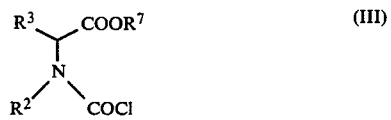

In cases where $R^2$ denotes hydrogen, an isocyanate of the formula (III-a) can form in this reaction, particularly at an elevated temperature.

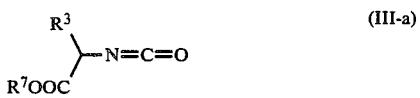

The compound of the formula (III) or (III-a) is reacted with a compound of the formula (IV) in which $R^8$ has one of the meanings of $R^7$ in formula (II) to give a compound of the formula (Ia).

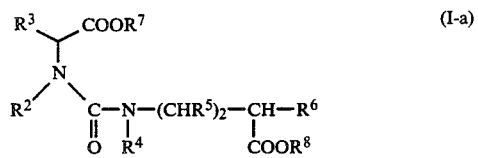

In cases where $R^7$ and $R^8$ denote alkyl or phenyl, if desired, a compound of the formula (I-a) can be hydrolyzed to give a compound of the formula (I-b).

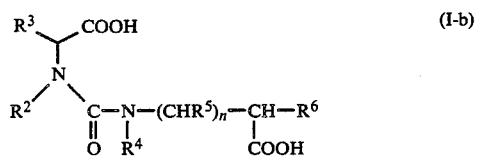

If $R^7$ in formula (I-a) denotes benzyl or 4-nitrobenzyl, a compound of the formula (I-a) can be converted into a compound of the formula (I-c) by hydrogenolysis.

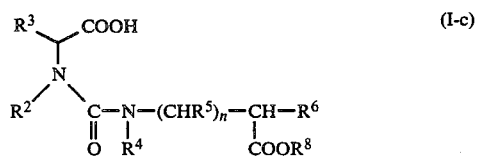

The reaction of the compound of the formula (II) with phosgene is carried out in an aprotic organic solvent, with or without the addition of an acid-binding agent; suitable acid-binding agents are basic compounds, in particular organic nitrogen bases, for example, triethylamine, tripropylamine, N-methylmorpholine, pyridine and the like. Examples of suitable solvents are methylene chloride, chloroform, tetrahydrofuran and dioxane. The reaction is carried out at a temperature which is low to slightly elevated, in general between −50° C. and +40° C., preferably at −30° C. to 0° C.

The reaction of a compound of the formula (III) with a compound of the formula (IV) is carried out under similar conditions but at a somewhat higher temperature, for instance 0° C. to 80° C., preferably 30° C. to 50° C. Apart from the solvents mentioned, dimethylformamide is also very suitable.

The reaction of a compound of the formula (IV) with an isocyanate of the formula (III-a) is carried out in a corresponding manner.

Hydrolysis of a compound of the formula (I-a) to give a compound of the formula (I-b) can be carried out by various means. In cases in which $R^7$ and $R^8$ in formula (I-a) denote alkyl, but not t-butyl, the reaction can advantageously be carried out with an alkali metal hydroxide or carbonate in a mixture of water and a lower alcohol. A suitable temperature is 0° C. to 100° C., preferably 20° C. to 40° C.

In cases in which $R^7$ and $R^8$ denote t-butyl, the reaction is carried out with the aid of an acid, preferably a strong acid, such as trifluoroacetic acid, hydrochloric acid or sulfuric acid, without adding a solvent or in methanol or ethanol at 0° to 80° C., preferably at 20° C. to 40° C.

In cases in which either $R^7$ or $R^8$ denotes t-butyl and the other radical denotes alkyl or phenyl, the processes described above can also be carried out sequentially in any desired sequence. Catalytic hydrogenolysis of a compound of the formula (I-a) wherein $R^7$ denotes benzyl or 4-nitrobenzyl can be brought about in a lower alcohol as the solvent, with the addition of a catalyst.

Suitable catalysts for the hydrogenolysis are noble metal catalysts, such as palladium black, palladium on charcoal or platinum dioxide. The reaction is carried out at a slightly elevated temperature, for instance at 20° C. to 80° C., preferably at 20° C. to 40° C., and under a slightly raised pressure of hydrogen, for instance 1 to 50 atmospheres, preferably under 1 to 8 atmospheres.

In analogy to the process indicated for the preparation of compounds of the formula (III), a compound of the formula (IV) can also be reacted with phosgene to give a compound of the formula (V).

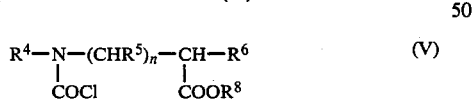

In cases where $R^4$ denotes hydrogen, an isocyanate of the formula (V-a)

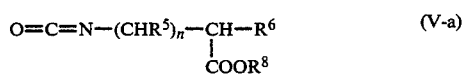

can be formed in this reaction, particularly at an elevated temperature.

A compound of the formula (V) or (V-a) is then reacted with a compound of the formula (II) under the conditions described above for the preparation of compounds of the formula (I-a) to give a compound of the formula (I-a).

The aminoacid esters of the formula (II) necessary as starting materials for this process are prepared from the corresponding aminoacids by customary methods (cf. the methods listed in Houben-Weyl/Müller, Methoden der Organischen Chemie (Methods of Organic Chemistry), volume 15/1, pages 315–370). If the relevant aminoacids do not occur naturally, as a rule they are readily accessible by synthesis.

Hexahydroazepine-2-carboxylic acid and its highers homologs are obtained from the lactam having the corresponding ring size by chlorination and Favorskii reaction with potassium tert.-butylate (J. Med. Chem. 14, 501 (1971)).

Tetrahydroisoquinoline-3-carboxylic acid and its substituted derivatives are readily accessible by a Pictet-Spengler reaction from the corresponding phenylalanine derivatives and formaldehyde (J. Amer. Chem. Soc. 70, 180 (1948)). Dihydroindole-2-carboxylic acid and its substituted derivatives are prepared in accordance with Aust. J. Chem. 20, 1,935 (1967).

From the latter two, the corresponding decahydroisoquinoline and octahydroindole derivatives respectively are obtained by hydrogenation under pressure on a rhodium catalyst. Again using Pictet-Spengler cyclization with formaldehyde, tetrahydroimidazo[2,3-c]pyridinecarboxylic acid is obtained from histidine (Hoppe-Seyler's Z. physiol. Chem. 284, 131 (1949)) and the thienopyridine derivatives are obtained from the corresponding thienoalanines (Heterocycles 16, 35 (1981)).

Thiazolidine-5-carboxylic acids substituted in the 2-position are easily obtained by a ring closure reaction from cysteine and the appropriate aldehyde (Japanese Patent No. 5 5011-547).

The starting materials of the formula (IV-a)

(corresponding to formula (IV) with n being 0), are obtained by esterification of the corresponding α-amino-acids under customary conditions (see above). Starting materials of the formula (IV-b)

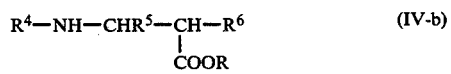

(corresponding to formula (IV) with n being 1), are obtained by addition of a primary amine of the formula (VI)

to an α-alkylenecarboxylate of the formula (VII)

The α-alkylenecarboxylates of the formula (VII) are readily accessible from the corresponding alkylated malonic acid hemiesters of the formula (VIII)

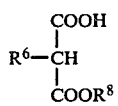

(VIII)

by Mannich reaction with formaldehyde and diethylamine (Arch. Pharm. 314, 197 (1981)).

The new compounds of the formula (I) have a long-lasting and strong hypotensive activity. This activity is developed by inhibition of the angiotensin converting enzyme (ACE). This enzyme converts the decapeptide angiotensin I into the octapeptide angiotensin II which has pressor activity; dysregulation of this enzymic reaction is a factor which induces various forms of hypertension in mammals and humans. Furthermore, ACE inactivates, by degradation, bradykinin, which has vasodepressor activity; this inactivation is also inhibited by the new compounds. Various groups have recently described compounds which are effective inhibitors of ACE (review, for example, J. Med. Chem. 24, 355 (1981)). The new compounds compete advantageously with the inhibitors described therein. In vitro, they inhibit the converting enzyme with $IC_{50}$ values of $5 \times 10^{-9}$ to $10^{-6}$ mole/l, and in vivo, on normotensive rats, the pressor reflex elicited by injection of angiotensin I is inhibited long-term by intravenous administration of doses at and above 0.1 mg/kg.

Because of these properties, the new compounds and their physiologically tolerated salts can be used to control high blood pressure of various etiologies by themselves or combined with other compounds which have hypotensive, vasodilator or diuretic activities. They can be used either alone or mixed with physiologically tolerated auxiliaries or vehicles.

The compounds can be administered orally or parenterally in an appropriate pharmaceutical formulation. For a form for oral use, the active compounds are mixed with the additives customary for this purpose, such as vehicles, stabilizers or inert diluents and converted by customary methods into suitable forms for administration, such as tablets, coated tablets, hard capsules, aqueous-alcoholic or oily suspensions or aqueous-alcoholic or oily solutions. Inert excipients which can be used are, for example, gum arabic, magnesium carbonate, potassium phosphate, lactose, glucose or starch, in particular corn starch. For this purpose, formulation can be as dry or as moist granules. Examples of suitable oily vehicles or solvents are plant and animal oils, such as sunflower oil or cod-liver oil.

For subcutaneous or intravenous administration, the active compounds or their physiologically tolerated salts are converted as desired, with the substances customary for this purpose, such as solubilizers, emulsifiers or other auxiliaries, into solutions, suspensions or emulsions. Examples of suitable solvents for the new active compounds and the corresponding physiologically tolerated salts are: water, physiological saline or alcohols, for example ethanol, propanediol or glycerol, in addition sugar solutions, such as glucose or mannitol solutions, and also a mixture of the various solvents mentioned.

The daily dose for compounds of the formula (I) and their salts is 20 mg to 3 g, preferably 50 mg to 1 g per patient. No toxic effects of the substances have been observed hitherto.

Unless another process is indicated, the compounds described in the following Examples were subjected to HPLC purification for analysis and biological determination.

Since all the compounds according to the invention have been prepared by only two methods, these two processes are to be presented in detail in four Examples in the following text. The other derivatives prepared analogously are compiled in a Table with their NMR data.

EXAMPLE 1

(3S)-<N-Isopropyl-N-(4-phenyl-2-carboethoxybutyl)-carbamoyl>-1,2,3,4-tetrahydroisoquinoline-3-carboxylic acid 1.1. Benzyl 1,2,3,4-tetrahydroisoquinoline-3-carboxylate benzenesulfonate 53 g (0.3 mole) of 1,2,3,4-tetrahydroisoquinoline-3-carboxylic acid, 150 ml of benzyl alcohol and 53.3 g (0.33 mole) of benzenesulfonic acid were heated at 140° C. for 1 hour, then 100 ml of toluene were added and the mixture was boiled under a water separator until the theoretical amount of water had formed. Thereafter, the solvent was removed, the residue was digested with ether, the precipitate was filtered off with suction and recrystallized from ethanol/ether.

Melting point 165°–166° C.

$[\alpha]_D -42.1°$, c=1 (DMF)

1.2. Benzyl N-chlorocarbonyl-1,2,3,4-tetrahydroisoquinoline-3-carboxylate 4.25 g of the above benzyl ester benzenesulfonate were dissolved in 100 ml of saturated sodium bicarbonate solution and this was extracted with methylene chloride, dried over sodium sulfate and the solvent was removed. The residue (2.67 g/0.01 mole) was dissolved, together with 1.5 g (0.015 mole) of triethylamine, in 10 ml of dry methylene chloride. The solution was added dropwise at −20° to −30° C. to 11.5 ml of a 15% strength solution of phosgene in methylene chloride, the mixture was stirred for 30 minutes and then evaporated to dryness.

1.3. Diethyl phenethylmalonate 45 g of diethyl malonate and 30 g of phenethyl bromide were mixed and added dropwise, cooling in ice, to a solution of sodium ethylate prepared from 6.5 g of sodium and 130 ml of absolute ethanol. The mixture was then boiled under reflux for 6 hours and allowed to cool down overnight. The major part of the ethanol was removed in vacuo, the residue was taken up in water, extracted with ether, this was dried over $Na_2SO_4$, evaporated and distilled.

Boiling point$_{0.1}$ 90° C.

1.4. Ethyl 2-methylene-4-phenylbutyrate 26.6 g (0.1 mole) of diethyl phenethylmalonate were added dropwise in the course of an hour, with stirring, to 5.6 g of KOH in 65 ml of absolute ethanol, the mixture was stirred at room temperature for 15 hours and then boiled for 5 minutes. The ethanol was removed in vacuo, ice-water was added and the mixture was extracted with ether. The aqueous phase was acidified with 2N hydrochloric acid and extracted with ether. The second extract was dried and evaporated and then neutralized with 8.8 ml of diethylamine. 12 ml of 30% strength formaldehyde solution were added, the mixture was stirred for 3 hours, then saturated with potassium carbonate, extracted with ether, the extract was washed with dilute hydrochloric acid, dried and evaporated.

NMR (CDCl₃) δ=7.05 s (5H); 6.02 s (1H); 5.4 s (1H); 4.15 q (4H); 2.65 bs (4H); 1.25 t (3H).

1.5.
N-Isopropyl-N-(2-carboethoxy-4-phenylbutyl)amine 14.2 g of ethyl 2-methylene 4-phenylbutyrate and 5.7 ml of isopropylamine were stirred in 25 ml of absolute ethanol at room temperature for 12 days, the solvent was removed, the residue was taken up in 1N hydrochloric acid, extracted with ether and the aqueous phase was made alkaline with sodium carbonate, extracted with ether and this was dried and evaporated.

NMR (CDCl₃): δ=7.1 s (5H), 4.1 q (2H); 3.0–2.2 m (6H); 2.05–1.5 m (3H); 1.22 t (3H); 1.0 d (6H).

1.6. Benzyl (3S)-<N-isopropyl-N-(4-phenyl-2-carboethoxybutyl)-carbamoyl>-1,2,3,4-tetrahydroisoquinoline-3-carboxylate The crude benzyl N-chlorocarbonyl-1,2,3,4-tetrahydroisoquinoline-3-carboxylate (from 1.2) was taken up in 10 ml of CH₂Cl₂, a solution of 2.6 g of N-isopropyl-N-(2-carboethoxy-4-phenylbutyl)amine and 1.2 ml of triethylamine in 10 ml of methylene chloride were added dropwise and the mixture was heated at 35° C. for 20 hours, then evaporated to dryness, the residue was taken up in ethyl acetate, the solution was washed with 1N hydrochloric acid, saturated sodium bicarbonate solution and water, dried and evaporated. The crude product was separated into the two diastereomers of the product on silica gel.

Isomer 1: NMR: (CDCl₃) δ7.3–6.8 m (14H); 5.05 s+t (3H); 4.48 s (2H), 4.2–3.5 m (4H); 3.4–2.4 m (6H); 2.0–1.6 m (2H); 1.3–0.9 m (9H).

Isomer 2: NMR (CDCl₃) δ7.3–6.9 m (14H); 5.0 s (2H); 4.8 t (1H); 4.52 s (2H); 4.2–3.5 m (4H); 3.3–2.4 m (6H); 2.0–1.6 m (2H), 1.3–1.0 m (9H).

1.7.
(3H)-<N-Isopropyl-N-(4-phenyl-2-carboethoxybutyl)-carbamoyl>-1,2,3,4-tetrahydroisoquinoline-3-carboxylic acid

1.7.1 Isomer 1

1.35 g of 1.6 (isomer 1) were hydrogenated in 30 ml of absolute ethanol with 0.7 g of Pd/C (10% strength) under 1 atmosphere pressure of hydrogen for 4 hours. After completion of uptake of hydrogen, the mixture was filtered and evaporated.

NMR δ=7.4–6.9 m (9H); 6.5 bs (1H); 4.66 t (1H); 4.4 s (2H); 4.2–3.5 m (3H); 3.4–2.3 m (7H); 2.0–1.6 m (2H); 1.3–0.9 m (9H).

Sodium salt: 0.35 g of 1.7.1 was taken up in 10 ml of H₂O, heated with 63 mg of sodium bicarbonate for 30 minutes, the mixture was evaporated and solidified with ether; colorless powder.

IR 1730, 1620 cm⁻¹.

1.7.2. Isomer 2

1.62 g of 1.6 (isomer 2) were hydrogenated in 30 ml of absolute ethanol with 0.7 g of Pd/C (10% strength) under 1 atmosphere pressure of hydrogen for 1.5 hours. After completion of uptake of hydrogen, the mixture was filtered and evaporated.

NMR=δ7.3–6.9 m (9H); 5.1 bs (1H); 4.60 t (1H); 4.30 s (2H); 4.2–3.5 m (3H); 3.3–2.4 m (7H); 2.0–1.5 m (2H); 1.4–1.0 m (9H).

Lysine salt: 0.57 g of 1.7.2. was dissolved in 10 ml of methanol, 0.21 g of lysine in 5 ml of water were added, the mixture was evaporated to dryness and solidified with ether, colorless powder.

IR 1730, 1610 cm⁻¹.

EXAMPLE 2
(3S)-<N-Isopropyl-N-(4-phenyl-2-carboxybutyl)-carbamoyl>-1,2,3,4-tetrahydroisoquinoline-3-carboxylic acid

2.1. Isomer 1

0.55 g of 1.7.1 was dissolved in 6 ml of ethanol, 6 ml of 6N sodium hydroxide solution were added and the mixture was allowed to stand overnight, the ethanol was removed, the residue was acidified with 1N hydrochloric acid, extracted with methylene chloride and this was dried over magnesium sulfate, evaporated and the residue was crystallized from chloroform/petroleum ether.

Melting point 118°–120° C.

NMR (DMSO)=δ7.1 s (9H); 4.5 t (1H); 4.43 s (2H); 4.0–2.8 m (7H); 1.9–1.5 m (2H), 1.05 dd (6H).

2.2. Isomer 2

0.68 g of 1.7.2 was dissolved in 10 ml of ethanol, 10 ml of 6N sodium hydroxide solution were added and the mixture was stirred for 2 hours, the ethanol was removed, the residue was acidified with 1N hydrochloric acid, extracted with methylene chloride, and this was dried and evaporated to a colorless foam.

NMR (CDCl₃)=δ7.0 s (9H); 4.65 t (1H); 4.44 s (2H); 4.0–3.0 m (7H), 2.1–1.6 m (2H); 1.1 dd (6H).

Bisdicyclohexylamine salt: 0.65 g of 2.2 was dissolved in 10 ml of methylene chloride, 0.6 ml of dicyclohexylamine was added, the mixture was evaporated and the residue was triturated with n-hexane; colorless crystals.

Melting point 67°–70° C. (decomposition).

IR 1630 cm⁻¹.

EXAMPLE 3
(3S)-<N-Methyl-N-(4-phenyl-2-carboethoxybutyl)-carbamoyl>-1,2,3,4-tetrahydroisoquinoline-3-carboxylic acid

3.1. N-Methyl-N-(2-carboethoxy-4-phenylbutyl)amine 26.3 g of ethyl 2-methylene-4-phenylbutyrate (1.4) and 4 g of methylamine in 150 ml of ethanol in an autoclave were heated at 80° C. for 10 hours. After cooling down, the ethanol was removed, the residue was taken up in 1N HCl, this was extracted with ether, made alkaline with sodium carbonate and again extracted, dried and evaporated.

NMR (CDCl₃)=7.1 s (5H); 4.1 q (2H); 3.1 s (3H); 3.0–2.2 m (6H); 2.0–1.5 m (2H); 1.22 t (3H).

3.2
N-Methyl-N-chlorocarbonyl-N-(2-carboethoxy-4-phenylbutyl)amine 2.35 g of 3.1 were dissolved in 10 ml of dry methylene chloride together with 1.5 g of triethylamine. This solution was added dropwise to 11.5 ml of a 15% strength solution of phosgene in methylene chloride at −20° to −30° C., the mixture was stirred for 30 minutes and then evaporated to dryness.

3.3. 2-Carbobenzoxy-3-carboxy-1,2,3,4-tetrahydroisoquinoline (Z-Tiq)

188 g (1.05 moles) of 1,2,3,4-tetrahydroisoquinoline-3-carboxylic acid were added to 1,050 ml of 1N NaOH at 0° and then at this temperature, 100 ml of benzyl chlorocarbonate and a further 1,050 ml of 1N NaOH were added dropwise simultaneously. The mixture was then stirred at room temperature for 2 hours, then extracted three times with ether and acidified with concentrated HCl to pH 1. The oil which separated out was extracted into ethyl acetate. The ethyl acetate solution was washed with water until the water phase had a pH of 3. After drying, the product crystallized on evaporation and scratching. 1.5 liters of diisopropyl ether were added and the mixture was stirred at room temperature for one hour. The product was then filtered off with suction; melting point 138°–139°.

3.4. Tert.-butyl ester of 2-carbobenzoxy-3-carboxy-1,2,3,4-tetrahydroisoquinoline 312 ml of tert.-butanol and 8 g of 4-dimethylaminopyridine were added to a solution of 248.8 g (0.8 mole) of 3.3 in 1.6 liters of methylene chloride. The mixture was cooled down to −5° C. and a solution of 176 g of dicyclohexylcarbodiimide in 350 ml of methylene chloride was added in portions. After 21 hours at room temperature, the precipitated dicyclohexylurea was filtered off with suction. The filtrate was extracted three times with saturated sodium bicarbonate solution. The organic phase was dried over magnesium sulfate and evaporated in vacuo at room temperature. A yellowish oil remained.

NMR: 7.3 s (5H); 7.2 s (4H); 5.1–4.3 m (3H); 5.0 s (2H); 1.46 s (9H).

3.5. Tert.-butyl ester of 3-carboxy-1,2,3,4-tetrahydroisoquinoline hydrochloride 284 g of 3.4. (0.775 mole) were dissolved in 3 liters of methanol, 15 g of 10% Pd-barium sulfate catalyst were added and the mixture was hydrogenated with hydrogen under normal pressure. The pH was maintained at 4.0 by dropwise addition of 1N methanolic HCl. When the uptake of hydrogen was complete, the mixture was filtered with suction, the filtrate was evaporated and the residue triturated with ether.

Melting point 180° C. (decomposition)

3.6 Tert.-butyl (3S)-<N-methyl-N-(4-phenyl-2-carboethoxybutyl)-carbamoyl>-1,2,3,4-tetrahydroisoquinoline-3-carboxylate 2.7 g of 3.5. were dissolved in 30 ml of saturated sodium bicarbonate solution, the solution was extracted with methylene chloride and the extract was dried and evaporated. The residue was dissolved in 10 ml of methylene chloride and 1.2 g of triethylamine and added dropwise to 3.2. in 10 ml of methylene chloride. The mixture was warmed at 35° C. for 20 hours, then evaporated to dryness and the residue was taken up in ethyl acetate, washed with saturated sodium bicarbonate solution, 1N HCl and water, dried over magnesium sulfate and evaporated; pale yellow resin.

NMR: 7.3–6.8 m (14H); 5.0 s (2H); 5.0–4.8 m (1H); 4.5 s (2H); 4.2–3.5 m (3H); 3.0 s (3H); 3.3–2.4 m (6H); 2.0–1.6 m (2H); 1.1 t (3H).

3.7. (3S)-<N-methyl-N-(2-carboethoxy-4-phenylbutyl)carbamoyl>-1,2,3,4-tetrahydroisoquinoline-3-carboxylic acid 3 g of 3.6. were stirred with 40 ml of trifluoroacetic acid at room temperature for 2 hours and then evaporated to dryness. The residue was taken up in ethyl acetate, washed three times with water, dried and evaporated.

NMR 7.4–6.9 m (9H); 6.8 bs (1H); 4.6 t (1H); 4.4 s (2H); 4.2–3.5 m (2H); 3.4–2.3 m (7H); 3.0 s (3H); 2.0–1.6 m (2H); 1.1 t (3H).

Lysine salt: colorless powder IR 1730, 1610 cm$^{-1}$.

EXAMPLE 4

(3S)-<N-Methyl-N-(2-carboxy-4-phenylbutyl)-carbamoyl>-1,2,3,4-tetrahydroisoquinoline-3-carboxylic acid 1.3 g of 3.7. were dissolved in 20 ml of ethanol, 20 ml of 6N sodium hydroxide solution were added, the mixture was stirred at room temperature for 3 hours, the ethanol was removed in vacuo and the residue was acidified with 1N hydrochloric acid, extracted with methylene chloride and dried over magnesium sulfate, and then evaporated.

NMR 7.6–6.9 m (9H); 6.0 bs (2H); 4.6 t (1H); 4.4 s (2H); 3.4–2.3 m (7H); 3.0 s (3H); 2.0–1.6 m (2H).

EXAMPLE 5

(3S)-<N-Ethyl-N-(4-phenyl-2S-carboethoxybutyl)-carbamoyl>-1,2,3,4-tetrahydroisoquinoline-3-carboxylic acid

5.1 N-Ethyl-N-(2-carboethoxy-4-phenylbutyl)amine 17 g of ethyl 2-methylene-4-phenylbutyrate (Example 1.4) and 3.6 g of ethylamine were dissolved in 50 ml of absolute ethanol and heated under 40 atmospheres of nitrogen at 105° C. for 20 hours. After the solvent had been removed, the residue was taken up in 5 normal hydrochloric acid, extracted with ether and the aqueous solution was adjusted to pH 9.5 with potassium carbonate, again extracted with ether, and this was dried with potassium carbonate and evaporated.

NMR (CDCl$_3$): 7.1 s (5H); 4.1 q (2H); 3.0–2.2 m (6H); 2.0–1.4 m (2H); 1.1 d+t (6H).

5.2. Benzyl (3S)-<N-ethyl-N-(4-phenyl-2-carboethexybutyl)carbamoyl>-1,2,3,4-tetrahydroisoquinoline-3-carboxylate 4.25 g of benzyl 1,2,3,4-tetrahydroisoquinoline-3-carboxylate benzenesulfonate were reacted with phosgene and 2.5 g of N-ethyl-N-(carboethoxy-4-phenylbutyl)amine by the process described in Example 1.2. and 1.6. After chromatography on silica gel (eluting with ethyl acetate/cyclohexane 1:5), 1.99 g of isomer 1 and 2.45 g of isomer 2 were obtained.

Isomer 1: NMR (CDCl$_3$) 7.3–6.8 m (14H); 5.05 s (2H); 4.95 t (1H); 4.48 s (2H); 4.2–3.5 m (4H); 3.4–2.4 m (6H); 2.0–1.6 m (3H); 1.1 t (6H);

Isomer 2: NMR (CDCl$_3$) 7.3–6.8 m (14H); 5.05 s (2H); 4.82 t (1H); 4.4 s (2H); 4.2–3.5 m (4H); 3.4–2.4 m (6H); 2.0–1.5 m (3H); 1.1 t (6H).

5.3.
(3S)-<N-Ethyl-N-(4-phenyl-2S-carboethoxybutyl)-carbamoyl>-1,2,3,4-tetrahydroisoquinoline-3-carboxylic acid 1.9 g of isomer 1 from Example 5.2. were hydrogenated by the process described in Example 1.7.

1H-NMR 7.4–6.9 m (9H); 6.5 bs (1H); 4.6 t (1H); 4.4 s (2H); 4.2–3.5 m (3H); 3.4–2.3 m (6H); 2.0–1.6 m (2H); 1.3–0.9 m (6H).

Lysine salt: 0.87 g of 5.3 was dissolved in 10 ml of methanol and 0.28 g of lysine in 5 ml of water was added. The solvent was removed and the residue was triturated with ether; colorless powder.

EXAMPLE 6
(2S)-<N-Ethyl-N-(4-phenyl-2S-carboethoxybutyl)-carbamoyl>-cis-endo-octahydroindole-2-carboxylic acid

6.1. Benzyl (2S)-cis-endo-octahydroindole-2-carboxylate hydrochloride 3 g of (2S)-cis-endo-octahydroindole-2-carboxylic acid (prepared according to European Patent Application No. 37,231) were added to a solution of 3 ml of thionyl chloride in 28.5 ml of benzyl alcohol prepared at −10° C. After 15 hours, the benzyl alcohol was distilled off and the product was triturated with diisopropyl ether, melting point 140° C.

6.2. Benzyl (2S)-<N-ethyl-N-(4-phenyl-2-carboethoxybutyl)-carbamoyl>-cis-endo-octahydroindole-2-carboxylate 2.96 g of the compound from Example 6.1 were reacted with phosgene and 2.5 g of the compound from Example 5.1 in accordance with the process described in Example 1.2 and 1.6. Separation of the diastereomers was carried out on silica gel using ethyl acetate/cyclohexane 1:4 as the eluant.

Isomer 1: $[\alpha]_D^{20} + 7.0°$ (c=1, CH$_3$OH).

1H-NMR (CDCl$_3$) 7.3 s (5H); 7.2 s (5H); 5.2–4.7 m (3H); 4.1 q (2H); 3.9–1.4 m (20H); 1.2 t (3H); 1.0 t (3H).

Isomer 2: $[\alpha]_D^{20} - 4.6°$ C. (c=1, CH$_3$OH).

1H-NMR (CDCl$_3$): 7.3 s (5H); 7.15 s (5H); 5.1 s (2H); 5.0–4.6 m (1H); 4.1 q (2H); 3.9–1.4 m (20H); 1.2 t (3H); 1.0 t (3H).

6.3. (2S)-<N-Ethyl-N-(4-phenyl-2S-carboethoxybutyl)-carbamoyl>-cis-endo-octahydroindole-2-carboxylic acid 1.5 g of the isomer 2 from Example 6.2 were hydrogenated by the process described in Example 1.7.

$[\alpha]_D^{20} + 23.3°$ (c=1, CH$_3$OH).

1H-NMR (CDCl$_3$) 7.15 s (5H); 4.5 m (1H); 4.1 q (2H); 3.9–1.4 m (20H); 1.0 t (6H).

Sodium salt: 0.876 g of 6.3 was dissolved in 10 ml of ethanol, 1.9 ml of 1N sodium hydroxide solution were added. The mixture was evaporated and triturated with ether; colorless powder.

EXAMPLE 7
(3S)-<N-Ethyl-N-(4-phenyl-2S-carboxybutyl)-carbamoyl>-1,2,3,4-tetrahydroisoquinoline-3-carboxylic acid 0.72 g of the compound from Example 5.3 was saponified with 10 ml of 6N sodium hydroxide solution by the process described in Example 2.

1H-NMR: 7.1 s (9H); 4.5 t (1H); 4.4 s (2H); 4.0–2.8 m (8H); 1.9–1.5 m (2H); 1.05 t (3H).

EXAMPLE 8
(2S)-<N-Ethyl-N-(4-phenyl-2S-carboxybutyl)-carbamoyl>-cis-endo-octahydroindole-2-carboxylic acid 0.39 g of the compound from Example 6.3 was saponified with sodium hydroxide solution by the process described in Example 2.

$[\alpha]_D^{20} + 15.8°$ (c=1, CH$_3$OH).

1H-NMR (CDCl$_3$) 7.15 s (5H); 4.5 m (1H); 3.9–1.4 m (20H); 1.0 t (3H).

Bisdicyclohexylamine salt: 0.31 g was dissolved in 10 ml of methylene chloride, 0.29 ml of dicyclohexylamine was added, the mixture was evaporated and triturated with diisopropyl ether; colorless powder.

EXAMPLE 9
<N-Ethyl-N-(4-phenyl-2-carboethoxybutyl)-carbamoyl>-cis-endo-2-azabicyclo[3.3.0]octane-3-carboxylic acid

9.1. Benzyl cis-endo-2-azabicyclo[3,3,0]octane-3-carboxylate hydrochloride

Prepared from cis-endo-2-azabicyclo[3.3.0]octane-3-carboxylic acid by the process described in Example 6.1.

9.2. Benzyl <N-ethyl-N-(4-phenyl-2-carboethoxybutyl)-carbamoyl>-cis-endo-2-azabicyclo[3.3.0]octane-3-carboxylate 2.82 g of the compound from Example 9.1 were reacted with phosgene and 2.5 g of the compound from Example 5.1 by the processes described in Example 1.2 and 1.6. Separation of the diastereomers was carried out on silica gel using ethyl acetate/cyclohexane (1:3) as eluant.

Isomer 1 1H-NMR (CDCl$_3$): 7.3 s (5H); 7.2 s (5H); 5.3–4.7 m (3H); 4.1 q (2H); 3.9–1.4 m (18H); 1.2 t (3H); 1.05 t (3H).

Isomer 2 1H-NMR (CDCl$_3$): 7.3 s (5H); 7.15 s (5H); 5.1 s (2H); 4.8 m (1H); 4.15 q (2H); 4.0–1.5 m (18H); 1.15 t (3H); 1.0 t (3H).

9.3.
<N-Ethyl-N-(4-phenyl-2-carboethoxybutyl)-carbamoyl>-cis-endo-2-azabicyclo[3.3.0]octane-3-carboxylic acid Prepared from 1 g of isomer 2 from Example 9.2 by the process described in Example 6.2.

1H-NMR (CDCl$_3$) 7.1 s (5H); 4.4 m (1H); 4.1 q (2H); 3.8–1.4 m (18H); 1.0 t (6H).

EXAMPLE 10
<N-Ethyl-N-(4-phenyl-2-carboxybutyl)-carbamoyl>-cis-endo-2-azabicyclo[3.3.0]octane-3-carboxylic acid Prepared from 0.32 g of the compound from Example 9.3 by the process described in Example 5.3.

1H-NMR (CDCl$_3$) 7.1 s (5H); 4.5 m (1H); 3.8–1.4 m (18H); 1.0 t (3H).

The compounds listed in the following table were prepared by analogous processes using the appropriate starting materials.

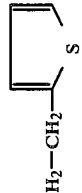

| n | R¹ | R¹' | R² | R³ | R⁴ | R⁵ | R⁶ | |
|---|----|-----|----|----|----|----|----|---|
| 11 | 0 | H | H | H | CH₃ | CH₃ | — | CH₂CH₂C₆H₅ | 7.2s(5H); 4.7-4.4m(1H); 3.8-2.8m (3H); 3.02s(3H); 2.0-1.7m(2H); 1.2d(5H) |
| 12 | 1 | H | H | H | CH₃ | C₂H₅ | H | CH₂CH₂C₆H₅ | 7.2s(5H); 4.7-4.4m(1H); 3.5-2.8m (7H); 2.0-1.7m(2H); 1.2d + t(6H) |
| 13 | 1 | H | C₂H₅ | H | CH₃ | CH₃ | H | CH₂CH₂C₆H₅ | 7.2s(5H); 4.7-4.4m(1H); 4.2q(2H) 3.5-2.8m(7H); 2.0-1.7m(2H); 1.2d + t(9H) |
| 14 | 1 | H | H | H | (CH₃)₂CH | CH₃ | H | CH₂CH₂C₆H₄—4-OCH₃ | 7.0-6.5m(4H); 4.8-4.4m(1H); 3.5-2.8m(5H); 3.02s(3H); 1.9-1.3m(3H); 1.2-0.9d(6H) |
| 15 | 0 | H | H | H | (CH₃)₂CH | CH₃ | — | CH₂CH₂C₆H₅ | 7.2s(5H); 4.8-4.3m(2H); 3.8-2.9m (2H); 2.0-2.0m(2H); 1.8-1.3m(3H); 1.3-0.9m(9H) |
| 16 | 0 | H | C₂H₅ | H | (CH₃)₂CH | C₂H₅ | — | CH₂CH₂C₆H₅ | 7.2s(5H); 4.8-4.3m(2H); 4.1q(2H) 3.9-2.9m(2H); 2.8-2.0m(2H); 1.8-1.3m(3H); 1.3-0.9m(12H) |
| 17 | 1 | H | H | CH₃ | (CH₃)₂CH | CH(CH₃)₂ | H | CH₂CH₂C₆H₅ | 7.2s(5H); 4.7-4.4m(1H); 3.8-2.8m(4H); 3.0s(3H); 2.0-1.7m(2H); 1.6-1.3m(3H); 1.2-0.9m(12H) |
| 18 | 1 | H | H | H | (CH₃)₂CHCH₂ | 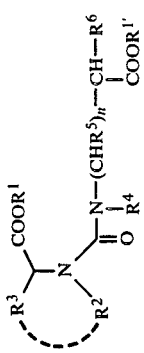 | H | CH₂—CH₂—C₆H₄—4-F | 7.2-6.9m(4H); 4.7-4.4m(1H); 3.8-2.6m(4H); 2.8-2.0m(2H); 1.9-1.4m(5H); 1.2-0.6m(10H) |
| 19 | 1 | H | C₂H₅ | H | (CH₃)₂CHCH₂ | 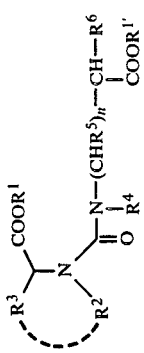 | H | CH₂CH₂—C₆H₄—4-F | 7.2-6.9m(4H); 4.7-4.4m(1H); 4.2q(2H)3.8-2.6m(4H); 2.8-2.0m(2H); 1.9-1.4m(5H); 1.2-0.6m + t(13H) |
| 20 | 1 | H | H | CH₃ | (CH₃)₂CHCH₂ | HC≡C—CH₂ | H | CH₂—CH₂—C₆H₃—(OCH₃)₂-3.4 | 6.8-6.4m(3H); 4.7-4.4m(1H); 4.2q(2H) 3.9s(6H); 3.0s(3H); 2.8-2.0m(2H); 1.9-1.4m(6H);1.1-0.9m(6H) |
| 21 | 0 | H | H | H | (CH₃)₂CHCH₂ | CH₃CH₂CH₂ | — | CH₂—CH₂—C₆H₄—4-F | 7.2-6.9m(4H); 4.7-4.4m(2H); 3.8-2.6m (2H); 2.8-2.0m(2H); 2.0-1.4m(7H); 1.1d + t(9H) |
| 22 | 1 | H | H | H | CH(CH₃)CH₂CH₃ | C₂H₅ | H | CH₂—CH₂—C₆H₄—2-CH₃ | 7.2s(4H); 4.7-4.4m(1H); 3.8-2.6m(5H); 2.8-2.0m (2H); 2.2s(3H); 1.9-1.4m(5H); 1.1d + 2t(9H) |
| 23 | 1 | H | C₂H₅ | H | CH(CH₃)CH₂CH₃ | C₂H₅ | H | CH₂—CH₂—C₆H₄—2-CH₃ | 7.2s(4H); 4.7-4.4m(1H); 4.2q(2H); 3.8-2.6m (5H); 2.8-2.0m(2H); 2.2s(3H); 1.9-1.4m(5H); 1.3-0.9m(12H) |
| 24 | 1 | H | H | H | CH₂CONH₂ | C₂H₅ | H | CH₂—CH₂—[thiophene] | 7.3-6.9m(3H); 4.7-4.4m(1H); 3.8-2.6m(5H); 2.8-2.0m(4H); 1.9-1.4m(2H); 1.0t(3H) |

4,624,962

-continued

| | | | | | | |
|---|---|---|---|---|---|---|
| 25 | 1 | H | C₂H₅ | CH₂CONH₂ | C₂H₅ | H | 7.3–6.9m(3H); 4.7–4.4m(1H); 4.2q(2H); 3.8–2.6m(5H); 2.8–2.0m(4H); 1.9–1.4m(2H)1.2t(3H); 1.0t(3H) |
| 26 | 0 | H | H | CH₂CONH₂ | C₂H₅ | — | 7.6–7.0m(4H); 4.8–4.3m(2H); 4.2q(1H); 2.8–2.0m(4H); 1.9–1.4m(2H); 1.2t(3H) |
| 27 | 1 | H | C₂H₅ | CH₂CH₂COOH | CH₃ | H | 7.2s(5H); 4.7–4.4m(1H); 3.6–2.8m(3H); 2.8–2.0m(4H); 2.0s(3H);1.8–1.4m(4H) |
| 28 | 1 | H | H | CH₂CH₂CONH₂ | CH₃ | H | 7.2s(5H); 4.7–4.4m(1H); 3.6–2.8m(3H); 2.8–2.0m(4H); 2.0s(3H)1.8–1.4m(4H) |
| 29 | 1 | H | C₂H₅ | CH₂CH₂CONH₂ | C₂H₅ | H | 8.6–7.2m(4H); 4.7–4.4m(1H); 4.2q(2H); 3.6–2.8m(5H); 2.8–2.0m(4H); 1.8–1.4m(4H); 1.22t(6H) |
| 30 | 1 | H | H | (CH₂)₄NH₂ | 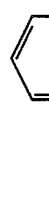 | H | 7.25(5H); 4.7–4.4m(1H); 3.6–2.8m(5H); 2.8–2.0m(4H); 1.9–1.3m(8H); 1.1t(3H) |
| 31 | 1 | H | C₂H₅ | (CH₂)₄NH₂ | 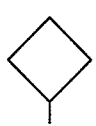 | CH₃ | 7.2s(5H); 4.7–4.4m(1H); 3.6–2.8m(4H); 2.8–2.0m(4H); 4.2(2H); 1.9–1.1m(14H)1.2–1.02t + d(9H) |
| 32 | 1 | H | H | CH₂SH | —CH₂—CH=CH₂ | H | 7.2s(4H); .8m(1H); 5.0–4.3m(5H); 3.6–2.7m(3H); 2.8–2.0m(4H)2.1s(3H); 1.9–1.4m(2H) |
| 33 | 1 | CH₃ | H | CH₂SH | —CH₂CH₂CH₃ | H | 7.1–6.7m(4H); 4.8–4.3m(1H); 3.6–2.7m(5H); 2.8–2.0m(4H); 2.0s(3H); 1.9–1.4m(4H); 1.1t(3H) |
| 34 | 0 | H | H | CH₂SH | —C₂H₅ | — | 7.2s(5H); 4.0–4.3m(2H); 4.2q3.8–2.8m(2H); 2.8–2.0m(4H); 1.9–1.4m(2H); 1.2t(3H) |
| 35 | 1 | H | C₂H₅ | CH₂SC₆H₅ | —C₂H₅ | H | 7.2s(10H); 4.8–4.3m(1H); 3.8–2.8m(6H); 3.4–2.8m(1H); 1.9–1.4m(2H)1.1t(3H) |
| 36 | 1 | H | H | CH₂SC₆H₅ | —C₂H₅ | H | 7.2s(10H); 4.8–4.3m(1H); 4.2q(2H); 3.8–2.8m(6H); 3.4–2.8m(2H); 1.9–1.4m(2H); 1.3–1.0m(6H) |
| 37 | 1 | H | C₂H₅ | CH₂CH₂SCH₃ | —CH₃ | H | 7.2s(5H); 4.7–4.4m(1H); 3.8–2.8m(3H); 2.8–2.0m(4H); 2.2s(3H); 2.1s(3H); 1.9–1.4m(4H) |
| 38 | 1 | H | H | CH₂CH₂SCH₃ | —C₂H₅ | H | 6.8–6.3m(3H); 4.7–4.4m(1H); 4.2q(2H); 4.0s(6H); 3.8–2.8m(4H);2.8–2.0m(4H); 2.2s(3H); 1.9–1.4m(4H) |
| 39 | 1 | H | CH₃ | CH₂CH₂SCH₃ | —CH₂CH₂CH₃ | CH₃ | 7.2s(5H); 4.7–4.4m(1H); 3.8–2.8m(3H); 2.8–2.0m(4H); 2.2s(3H)2.0s(3H)1.9–1.4m(6H); 1.0d + t(6H) |
| 40 | 0 | H | H | CH₂CH₂SCH₃ | —CH₂CH₂CH₃ | — | 7.2s(5H); 4.8–4.3m(2H); 4.2q(2H); 3.8–2.8m(2H); 2.8–2.0m(4H)2.2s(3H); 1.9–1.4m(6H); 1.2t(3H)1.0t(3H) |
| 41 | 1 | H | H | CH₂C₆H₅ | CH₃ | H | 7.2s(5H); 4.7–4.3m(1H); 3.8–2.6m(3H); 2.8–2.0m(3H); 1.9–1.3m(6H); 1.2t(3H) |
| 42 | 1 | H | H | CH₂C₆H₅ | C₂H₅ | H | 7.2–6.9m(10H); 4.7–4.3m(1H); 3.8–2.6m(6H); 2.8–2.0m(2H); 1.0t(3H) |
| 43 | 1 | H | H | CH₂C₆H₅ | C₂H₅ | H | 7.4–6.9m(10H); 4.7–4.3m(1H); 3.8– |

2.6m(6H); 2.8-2.0m(2H); 1.0t(3H)

| No. | n | | | | | | | NMR |
|---|---|---|---|---|---|---|---|---|
| 44 | 1 | H | C₂H₅ | H | CH₂C₆H₅ | CH₂—CH═CH₂ | CH₂—NH—C₆H₅ | CH₃ | 7.1-6.4m(10H); 5.8m(1H); 4.8-4.3m(5H); 4.2q(2H); 3.8-2.6m(5H);2.8-2.0m(2H); 1.3t(3H) |
| 45 | 1 | H | H | CH₃ | CH₂C₆H₅ | cyclopentyl | H | | 8.0s(1H); 7.8-6.9m(10H); 4.7-4.3m(1H); 3.9-2.8m(4H); 2.8-2.0m(4H); 2.1s(3H); 1.9-1.4m(10H) |
| 46 | 1 | H | C₂H₅ | H | CH₂C₆H₅ | CH(CH₃)₂ | [2-(NH)indolyl-CH₂CH₂-] | H | 7.3-6.9m(6H); 4.7-4.4m(1H); 4.2q(2H); 3.8-2.6m(4H); 2.7s(3H); 2.3s(3H); 2.8-2.0m(4H); 1.3t(3H); 1.1d(6H) |
| | | | | | | | [=N-N(CH₃)₂ hydrazone, CH₂CH₂-] | | |
| 47 | 1 | H | H | H | CH₂C₆H₅ | C₂H₅ | CH₂CH₂—C₆H₅ | H | 7.2s(10H); 4.7-4.4m(1H); 3.8-2.6m(5H); 2.8-2.0m(4H); 1.9-1.4m(2H); 1.1t(3H) |
| 48 | 0 | H | H | H | CH₂C₆H₅ | C₂H₅ | CH₂CH₂—C₆H₅ | H | 7.2s(10H); 4.8-4.3m(2H); 3.8-2.6m (2H); 1.9-1.4m(2H); 1.2t(3H) |
| 49 | 0 | H | C₂H₅ | H | CH₂C₆H₅ | CH₂CH₂CH₃ | CH₂CH₂—C₆H₄—4-F | H | 7.3-6.9m(9H); 4.8-4.3m(2H); 3.8-2.6m(2H); 4.2q(2H); 1.9-1.4m(4H); 1.2t(3H); 1.0t(3H) |
| 50 | 0 | H | C₂H₅ | H | CH₂C₆H₅ | CH₂—CH═CH—CH₃ | CH₂CH₂—C₆H₅ | H | 7.2s(10H); 5.5-5.1m(2H); 4.8-4.1m(4H); 4.2q (2H); 2.8-2.0m(4H); 2.2d(3H); 1.9-1.4m(2H); 1.2t(3H) |
| 51 | 1 | H | H | H | [CH₂-imidazolyl(NH)] | CH₃ | CH₂CH₂C₆H₅ | H | 7.6d(1H); 6.7d(1H); 7.2s(5H); 4.7-4.3m(1H); 3.8-2.6m(3H); 2.3s(3H); 2.8-2.0m(4H); 1.9-1.4m(2H) |
| 52 | 1 | H | C₂H₅ | H | " | C₂H₅ | CH₂CH₂C₆H₅ | H | 7.6d(1H); 7.2s(5H); 6.7d(1H); 4.7-4.3m(1H); 4.2q(2H); 3.8-2.6m(5H); 2.8-2.0m(4H); 1.9-1.4m(2H);1.2t(3H) |
| 53 | 1 | H | H | H | CH₂OH | CH₃ | CH₂CH₂C₆H₅ | H | 7.2s(5H); 4.7-4.3m(1H); 2.2s(3H); 3.8-2.6m(2H); 2.8-2.0m(2H); 1.9-1.4m(2H) |
| 54 | 1 | H | C₂H₅ | H | CH₂CH | C₂H₅ | CH₂CH₂—C₆H₄—4-OCH₃ | H | 6.9-6.5m(4H); 7.2s(5H); 4.7-4.3m(1H); 4.2q(3H); 4.0s(3H); 3.8-2.6m(7H); 2.8-2.0m(2H); 1.9-1.4m(2H); 1.0t(3H); 1.1t(3H) |
| 55 | 1 | H | H | H | CH₂OCH₃ | CH(CH₃)₂ | CH₂C₆H₅ | H | 7.2s(5H); 4.7-4.3m(1H); 3.9-2.6m + s(9H); 2.8-2.0m(2H); 1.1d(6H) |
| 56 | 1 | H | H | H | CH₂OCH₃ | CH(CH₃)₂ | CH₃ | H | 4.7-4.3m(1H); 3.9-2.6m + s(9H); 1.2d(9H) |
| 57 | 1 | H | H | H | CH₂OCH₃ | CH(CH₃)₂ | H | H | 4.7-4.3m(1H); 3.9-2.6m + s(9H); 2.4-2.0m (2H); 1.2d(6H) |

| # | | | | | | | | | NMR |
|---|---|---|---|---|---|---|---|---|---|
| 58 | 1 | H | C₂H₅ | H | | CH₃ | H | CH₂CH₂C₆H₅ | 8.0s(1H); 7.8–6.8m(10H); 4.7–4.3m(1H); 4.2q(2H); 3.8–2.7m(3H); 2.8–2.0m(4H); 1.9–1.3m(2H); 2.0s(3H)1.2t(3H) |
| 59 | 1 | H | H | H | | C₂H₅ | H | —CH₂ | 8.0s(1H); 7.8–6.8m(10H); 4.7–4.3m(1H); 3.8–2.7m(5H); 2.8–2.0m(4H); 1.9–1.3m(2H); 1.1t(3H) |
| 60 | 1 | H | H | H | CH₂CH₂OCH₃ | CH₃ | H | CH₂CH₃ | 4.7–4.3m(1H); 3.8–2.7m + s(8H); 2.3s(3H); 1.9–1.4m(4H); 1.1t(3H) |
| 61 | 1 | H | C₂H₅ | CH₃ | CH₂CH₂OCH₃ | CH₂—CH=CH₂ | H | CH₂CH(CH₃)₂ | 5.8m(1H); 4.9–4.1m(5H)1.9–1.4m(5H); 4.2q(2H)1.9–1.4m(5H); 1.0d(9H) |
| 62 | 0 | H | C₂H₅ | H | CH₂CH₂OCH₃ | C₂H₅ | — | CH₂CH₂C₆H₅ | 7.2m(5H); 4.9–4.3m(2H); 3.7–2.9m + s(7H); 4.2q(2H); 2.8–2.0m(2H)1.9–1.4m(4H); 1.3t(3H); 1.0t(3H) |
| 63 | 1 | H | H | CH₃ | (CH₂)₄NHCOCH₃ | CH₃ | H | CH₂CH₂C₆H₅ | 7.2s(5H); 4.7–4.4m(1H); 3.7–2.9m(2H); 2.8–2.0m(4H); 2.1s(9H); 1.9–1.3m(8H); 1.1d(3H) |
| 64 | 1 | H | C₂H₅ | H | (CH₂)₄NHCOCH₃ | CH(CH₃)₂ | H | (CH₂)₄CH₃ | 4.7–4.4m(1H); 4.2q(2H); 3.7–2.9m(6H); 2.0–1.2m(14H); 1.3t(3H); 1.1–0.9m(9H) |
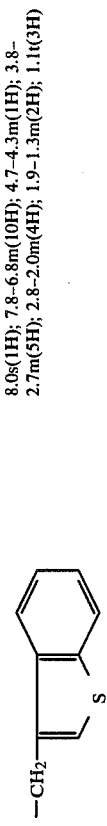

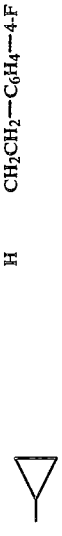

| | n | R¹ | R¹' | R²−R³ | R⁴ | R⁵ | R⁶ | NMR |
|---|---|---|---|---|---|---|---|---|
| 65 | 1 | H | H | (CH₂)₃ | CH₃ | H | CH₂CH₂C₆H₅ | 7.2s(5H); 4.9–4.4m(1H); 3.8–2.9m(5H); 2.8–2.0m(2H); 2.0s(3H); 1.9–1.4m(6H) |
| 66 | 1 | H | H | (CH₂)₃ | C₂H₅ | H | CH₂C₆H₅ | 7.2s(5H); 4.9–4.4m(1H); 3.8–2.9m(7H); 2.8–2.0m(2H); 1.9–1.4m(4H)1.1t(3H) |
| 67 | 1 | H | H | (CH₂)₃ | CH(CH₃)₂ | H | CH₂CH₂CH₃ | 4.8–4.4m(1H); 3.8–2.9m(6H); 1.9–1.3m(10H); 1.2–0.9m(9H) |
| 68 | 1 | H | H | (CH₂)₃ | CH₂−CH=CH₂ | H | CH₁−CH₂−CH(CH₃)₂ | 5.8m(1H); 4.8–4.2m(5H); 3.8–2.9m(5H); 1.9–1.3m(9H); 1.0d(6H) |
| 69 | 1 | H | H | (CH₂)₃ | CH₂−C≡CH | H | CH₁−CH₂−C(CH₃)₃ | 4.8–4.2m(1H); 3.8–2.9m(7H); 1.9–1.3m(9H); 0.9s(9H) |
| 70 | 1 | H | H | (CH₂)₃ |  | H | CH₂CH₂−C₆H₄−4-F | 7.3–6.8m(4H); 4.7–4.3m(1H); 3.8–2.7m(6H); 2.8–2.0m(2H); 1.9–1.3m(6H); 1.0–0.6m(4H) |
| 71 | 1 | H | H | (CH₂)₃ | −C₂H₅ | H | CH₂−CH₂−C₆H₃−2,6-Cl₂ | 7.3s(3H); 4.7–4.3m(1H); 3.7–2.7m(7H); 2.8–2.0m(2H); 1.9–1.3m(6H)1.1t(3H) |
| 72 | 1 | H | H | (CH₂)₃ | −C₂H₅ | H | 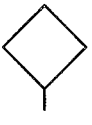 | 8.0s(1H); 7.6–6.7m(5H)4.7–4.3m(1H); 3.7–2.7m(7H); 2.8–2.0m(2H); 1.1t(3H) |
| 73 | 1 | H | C₂H₅ | (CH₂)₃ | CH₃ | H | CH₂CH₂C₆H₅ | 7.2s(5H); 4.7–4.3m(1H); 3.7–2.7m(5H); 4.2q(2H); 2.8–2.0m(2H); 2.1s(3H); 1.9–1.4m(6H); 1.3t(3H) |
| 74 | 1 | H | C₂H₅ | (CH₂)₃ | C₂H₅ | H | CH₂CH₂C₆H₅ | 7.2s(5H); 4.7–4.3m(1H); 4.2q(2H); 3.7–2.7m(7H); 2.8–2.0m(2H); 1.9–1.4m(6H); 1.3t(3H); 1.0t(3H) |
| 75 | 1 | H | C₂H₅ | (CH₂)₃ | CH(CH₃)₂ | H | CH₂CH₂C₆H₅ | 7.2s(5H); 4.7–4.3m(1H); 4.2q(2H); 3.7–2.7m(6H); 2.8–2.0m(2H); 1.9–1.3m(6H); 1.3t(3H); 0.9d(6H) |
| 76 | 1 | H | C₂H₅ | (CH₂)₃ | CH₂−CH=CH₂ | H | CH₂CH₂C₆H₅ | 7.2s(5H); 5.8m(1H); 4.8–4.1m(5H); 4.2q(2H); 3.7–2.7m(5H); 2.8–2.0m(2H); 1.9–1.4m(6H); 1.3t(3H) |
| 77 | 1 | H | C₂H₅ | (CH₂)₃ |  | H | CH₂CH₂C₆H₅ | 7.2s(5H); 4.6–4.2m(1H); 4.2q(2H); 3.8–2.7m(6H); 2.8–2.0m(2H); 1.9–1.4m(12H); 1.3t(3H) |

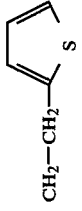

| # | | | | | | | NMR |
|---|---|---|---|---|---|---|---|
| 97 | 1 | H | H | (CH₂)₄ | C₂H₅ | ![2-methylbenzothiophene-CH₂] | H | 7.4-6.8m(5H); 4.7-4.4m(1H); 3.6-2.8m(7H); 2.8-2.0m(2H); 1.9-1.4m(6H); 1.0t(3H) |
| 98 | 1 | H | H | (CH₂)₄ | C₂H₅ | imidazole-CH₂CH₂- | H | 7.6d(1H); 6.7d(1H); 4.7-4.4m(1H); 3.6-2.8m(7H); 2.8-2.0m(2H); 1.9-1.4m(8H); 1.0t(3H) |
| 99 | 1 | H | C₂H₅ | (CH₂)₄ | CH₂—CH=CH₂ | CH₂—CH₂—C₆H₃—2,6-Cl₂ | H | 7.3s(3H); 5.8m(1H); 4.9-4.3m (5H); 4.2q(2H); 3.6-2.8m(5H); 2.8-2.0m(2H); 1.9-1.5m(8H) |
| 100 | 1 | H | H | (CH₂)₄ | CH₂—C≡CH | CH₂—CH₂—C₆H₃—Cl—2-OCH₃—4 | H | 7.3-6.6m(3H); 4.7-4.3m(1H); 3.8-2.8m(7H); 4.0s(3H); 2.8-2.0m(2H) 1.9-1.5m(9H) |
| 101 | 1 | H | C₂H₅ | (CH₂)₄ | CH₂—CH₃ | 1,3-dimethylpyrazole-CH₂CH₂- | CH₃ | 7.4s(1H); 4.7-4.3m(1H); 4.2q(2H) 3.8-2.8m(6H); 2.3s(3H); 2.1s(3H); 2.8-2.0m(2H); 1.9-1.4m(8H); 1.3t (3H); 1.0d(3H) |
| 102 | 1 | H | H | (CH₂)₄ | CH₃ | CH₂—C₆H₅—C₆H₅ | H | 7.4-6.8m(9H); 4.7-4.3m(1H); 3.8-2.8m(5H); 2.2s(3H); 2.8-2.0m(2H) 1.9-1.4m(6H) |
| 103 | 1 | H | C₂H₅ | (CH₂)₄ | cyclopentyl | CH₃ | H | 4.7-4.3m(1H); 4.2q(2H); 3.8-2.8m (6H); 1.9-1.3m(14H); 1.3t(3H); 1.0d(3H) |
| 104 | 1 | H | H | (CH₂)₄ | C₂H₅ | 2-phenylthiazole-CH₂CH₂- | H | 7.5s(1H); 7.1s(5H); 4.7-4.3m(1H) 3.8-2.8m(7H); 2.8-2.0m(2H); 1.9-1.4m(8H); 1.0t(3H) |
| 105 | 1 | H | H | (CH₂)₄ | C₂H₅ | CH₂CH₂CH₂C₆H₅ | H | 7.2s(5H); 4.7-4.3m(1H); 3.8-2.9m (7H); 2.8-2.0m(2H); 1.9-1.4m (10H); 1.0t(3H) |
| 106 | 0 | H | H | (CH₂)₄ | CH₃ | CH₂CH₂C₆H₅ | — | 7.2s(5H); 4.9-4.2m(2H); 3.8-2.9m (2H); 2.8-2.0m(2H); 2.2s(3H); 1.9-1.5m(8H) |
| 107 | 0 | H | H | (CH₂)₄ | C₂H₅ | CH₂—CH₂—C₆H₄—4-F | — | 7.2-6.8m(4H); 4.9-4.2m(2H); 3.8-2.9m(4H); 2.8-2.0m(2H); 2.0-1.5m (8H); 1.0t(3H) |
| 108 | 0 | H | C₂H₅ | (CH₂)₄ | CH(CH₃)₂ | CH₂—CH₂—C₆H₃—(OCH₃)₂—3,4 | — | 6.9-6.2m(3H); 4.9-4.2m(2H); 4.2q (2H); 4.0s(6H); 3.8-2.9m(3H); |

-continued

| | | | | | | |
|---|---|---|---|---|---|---|
| 109 | H | C₂H₅ | (CH₂)₄ | —CH₂—CH=CH₂ | — | 2.8-2.0m(2H); 1.9-1.4m(8H); 1.0d(6H); 1.3t(3H) |
| 110 | H | H | (CH₂)₅ | CH₃ | H | 7.2s(5H); 4.9-4.2m(6H); 4.2q(2H) 5.8m(1H); 2.8-2.1m(2H); 1.9-1.4m(8H); 1.3t(3H) |
| 111 | H | C₂H₅ | (CH₂)₅ | C₂H₅ | H | 7.2s(5H); 4.7-4.3m(1H); 3.8-2.8m(5H); 2.8-2.0m(2H); 2.3s(3H); 1.9-1.4m(10H) |
| 112 | H | H | (CH₂)₅ | CH(CH₃)₂ | H | 7.2s(4H); 4.7-4.3m(1H); 4.2q(2H) 3.8-2.8m(7H); 2.2s(3H); 2.8-2.0m(2H); 1.9-1.4m(10H) 1.3t(3H)1.1t(3H) |
| 113 | H | C₂H₅ | (CH₂)₅ | ⟨square⟩ | H | 7.1-6.5m(3H); 4.7-4.3m(1H); 3.8-2.8m(6H); 4.0s(3H); 2.8-2.0m(2H); 1.9-1.4m(10H); 1.1d(6H) |
| 114 | H | H | (CH₂)₅ | ⟨pentagon⟩ | H | 7.2s(5H); 4.7-4.4m(1H); 3.8-2.8m(6H); 4.2q(2H); 2.8-2.0m(2H); 1.9-1.4m(16H); 1.3t(3H) |
| 115 | H | H | (CH₂)₅ | CH₂—CH=CH—CH₃ | H | 7.2s(5H); 4.7-4.4m(1H); 3.8-2.8m(6H); 2.8-2.0m(2H); 1.9-1.4m(18H) |
| 116 | H | C₂H₅ | (CH₂)₅ | ⟨pyridyl-CH₂CH₂⟩ | H | 8.6-7.2m(4H); 5.8-5.4m(2H); 4.9-4.2m(5H); 3.8-2.9m(5H); 2.8-2.1m(2H); 1.9-1.4m + s(13H) |
| 117 | H | H | (CH₂)₅ | CH₃ | H | 7.2s(5H); 4.7-4.4m(1H); 4.2q(2H); 3.8-3.1m(7H); 2.9-2.4m(2H); 1.9-1.4m(11H); 1.1d(6H) |
| 118 | H | H | (CH₂)₅ | C₂H₅ | CH₃ | 4.7-4.4m(1H); 3.8-3.1m(4H); 2.2s(3H); 1.9-1.4m(14H); 1.0d + t(3H) |
| 119 | H | C₂H₅ | (CH₂)₅ | CH(CH₃)₂ | H | 4.7-4.4m(1H); 3.8-3.1m(7H); 1.9-1.4m(13H); 1.0d + t(9H) |
| 120 | H | H | ⟨naphthyl with ethyl substituents⟩ | CH₃ | H | 7.4-6.8m(5H); 4.7-4.4m(1H); 4.2q(2H); 3.8-3.0m(8H); 1.9-1.4m(8H); 1.3t(3H); 1.1d(6H) |
| 121 | H | C₂H₅ | " | CH₃ | H | 7.3-6.9m(8H); 4.7-4.2m(3H); 3.5-2.9m(3H); 2.8-2.3m(4H); 1.9-1.4m(2H); 2.2s(3H) |
| | | | | | | 7.3-6.9m(8H); 4.7-4.3m(3H); 4.2q(2H); 3.5-2.9m(3H); 2.8-2.3m(4H); 1.9-1.4m(2H); 2.2s(3H); 1.2t(3H) |

| | | | | | | |
|---|---|---|---|---|---|---|
| 122 | 1 | H | " | H | C₂H₅ | CH₂CH₂—C₆H₄—4-OCH₃ | 7.2–6.5m(8H); 4.7–4.3m(3H); 3.8–2.9m(5H); 4.0s(3H); 2.8–2.3m(4H); 1.9–1.4m(2H); 1.1t(3H) |
| 123 | 1 | C₂H₅ | " | H | C₂H₅ | CH₂CH₂—C₆H₄—4-OCH₃ | 7.3–6.5m(8H); 4.7–4.3m(3H); 4.2q(2H); 3.8–2.9m(5H); 4.0s(3H); 2.8–2.3m(4H); 1.9–1.4m(2H); 1.3t(3H); 1.1t(3H) |
| 124 | 1 | H | " | H | CH(CH₃)₂ | CH₂CH₂—C₆H₄—2-CH₃ | 7.2–6.8m(8H); 4.7–4.3m(3H); 4.0–2.9m(4H); 2.8–2.3m(4H); 2.3s(3H); 1.9–1.4m(2H); 1.0d(6H) |
| 125 | 1 | C₂H₅ | " | H | CH(CH₃)₂ | CH₂CH₂—C₆H₄—2-CH₃ | 7.2–6.8m(8H); 4.7–4.3m(3H); 4.2q(2H); 4.0–2.9m(4H); 2.8–2.3m(4H); 2.3s(3H); 1.9–1.4m(2H); 1.3t(3H); 1.0d(6H) |
| 126 | 1 | H | " | H | CH₂—CH=CH₂ | CH₂CH₂—CH(CH₃)₂ | 7.2s(4H); 5.8m(1H); 5.0–4.3m(7H); 3.5–2.9m(3H); 2.8–2.3m(2H); 1.9–1.4m(5H); 1.0d(6H) |
| 127 | 1 | H | " | H | CH₃ | CH₃ | 7.2s(4H); 4.7–4.3m(3H); 3.5–2.9m(3H); 2.8–2.3m(2H); 2.3s(3H); 1.1d(6H) |
| 128 | 1 | H | " | H |  | CH₂—S—C₆H₅ | 7.3–6.9m(9H); 4.7–4.3m(3H); 3.5–2.9m(6H); 1.1–0.6m(4H) |
| 129 | 1 | H | " | H | C₂H₅ | CH₂—CH₂—C₆H₄—4-N(CH₃)₂ | 7.2–6.4m(8H); 4.7–4.3m(3H); 3.5–2.9m(5H); 2.9s(6H); 2.8–2.3m(4H); 1.9–1.4m(2H); 1.1t(3H) |
| 130 | 1 | C₂H₅ | " | H | n-C₄H₉ | CH₂CH₂—C₆H₃—3-CN | 7.6–7.0m(8H); 4.7–4.3m(3H); 4.2q(2H); 3.8–2.9m(5H); 2.8–2.3m(4H); 1.9–1.4m(6H); 1.3t(3H); 1.0t(3H) |
| 131 | 1 | H | " | H | CH₂—CH₂—CH₃ |  CH₂—CH₂— | 8.6–7.2m(8H); 4.7–4.3m(3H); 3.8–2.9m(5H); 2.8–2.3m(4H); 1.9–1.4m(4H); 1.0t(3H) |
| 132 | 1 | H | " | H | CH₃ |  CH₂—CH₂— | 7.3–6.8m(8H); 4.7–4.3m(3H); 3.5–2.9m(3H); 2.3s(3H); 2.8–2.3m(4H); 1.9–1.4m(2H) |
| 133 | 1 | H | " | H |  |  CH₂—CH₂— | 8.0s(1H); 7.2s(4H); 4.7–4.3m(3H); 4.0–2.9m(4H); 2.9–2.3m(4H); 3.9s(3H); 1.9–1.2m(8H) |
| 134 | 1 | H | " | C₂H₅ | C₂H₅ | CH₂—CH₂—C₆H₃—(OCH₂O)—3.4 | 7.2–6.2m(7H); 5.0s(2H); 4.7–4.3m(3H); 4.2q(2H); 3.9–2.9m(5H); 2.9–2.3m(4H); 1.9–1.4m(2H); 1.3t(3H) |
| 135 | 1 | H | " | H | CH₃ | CH₂—CH₂—C₆H₄—O—C₆H₅—4 | 7.2–6.7m(13H); 4.7–4.3m(3H); 4.0–2.9m(2H); 2.9–2.3m(2H); 2.4s(3H); 1.9–1.4m(2H); 1.1d(3H) |

4,624,962

-continued

| # | | | | | NMR |
|---|---|---|---|---|---|
| 136 | 0 | H | H | CH₃ | CH₂—CH₂—C₆H₅ | 7.2s(9H); 4.7-4.3m(4H); 2.9-2.3m(4H); 2.3s(3H); 1.9-1.4m(2H) |
| 137 | 0 | H | C₂H₅ | CH₃ | CH₂—CH₂—C₆H₅ | 7.2s(9H); 4.7-4.3m(4H); 4.2q(2H); 2.9-2.3m(4H); 2.3s(3H)1.9-1.4m(2H); 1.3t(3H) |
| 138 | 0 | H | H | C₂H₅ | CH₂—CH₂—C₆H₄—4-F | 7.3-6.9m(8H); 4.7-4.3m(4H); 4.2q(2H); 3.6-2.9m(2H); 2.9-2.3m(4H); 1.9-1.4m(2H); 1.3t(3H); 1.0t(3H) |
| 139 | 0 | H | H | CH(CH₃)₂ | 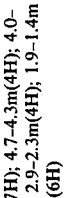 | 7.3-6.8m(7H); 4.7-4.3m(4H); 4.0-3.5m(1H); 2.9-2.3m(4H); 1.9-1.4m(2H); 1.1d(6H) |
| 140 | 0 | H | C₂H₅ | CH(CH₃)₂ | CH₂—CH₂—C₆H₃—(OCH₃)₂-3.4 | 7.3-6.2m(7H); 4.7-4.3m(4H); 4.2q(2H); 4.0-3.5m(1H); 4.0s(6H); 2.9-2.3m(4H); 1.9-1.4m(2H); 1.3t(3H); 1.1d(6H) |
| 141 | 0 | H | H | CH₂—CH=CH₂ | CH₂—CH₂—C₆H₄—2-Cl—4-OCH₃ | 7.2s(8H); 5.8m(1H); 5.0-4.2m(6H); 2.9-2.3m(4H); 2.2s(3H); 1.9-1.4m(2H) |
| 142 | 0 | H | C₂H₅ |  | CH₂CH₂—C₆H₅—2-Cl—4-OCH₃ | 7.2-6.6m(7H); 4.6-4.3m(4H); 4.2q(2H); 4.0-3.5m(1H); 4.0s(3H); 2.9-2.3m(4H); 1.9-1.3m(10H); 1.3t(3H) |
| 143 | 0 | H | H | C₄H₉ | CH₂CH₂—C₆H₃—2.6-Cl₂ | 7.4-6.8m(7H); 4.7-4.3m(4H); 3.8-3.1m(2H); 2.9-2.3m(4H); 1.9-1.4m(8H); 1.0t(3H) |
| 144 | 1 | H | H | CH₃ | CH₂—CH₂—C₆H₅ | 7.2-6.5m(8H); 4.7-4.3m(3H); 4.0s(3H); 3.5-2.9m(3H); 2.8-2.3m(4H); 1.9-1.4m(2H); 2.2s(3H) |
| 145 | 1 | H | H | CH₃ | CH₂—CH₂—C₆H₅ | 7.2-6.5m(8H); 4.7-4.3m(3H); 4.2q(2H); 4.0s(3H); 3.6-2.9m(5H); 2.8-2.3m(4H); 1.9-1.4m(2H); 1.2t(3H) |
| 146 | 1 | H | C₂H₅ | C₂H₅ | CH₂CH₂—C₆H₄—4-F | 7.3-6.5m(7H); 4.7-4.3m(3H); 4.0s(3H); 3.6-2.9m(5H); 1.9-1.4m(4H); 1.0t(3H) |
| 147 | 1 | H | H | CH(CH₃)₂ | CH₂—CH₂—C₆H₄—2-CH₃ | 7.3-6.5m(7H); 4.7-4.3m(3H); 4.2q(2H); 4.0s(3H); 4.0-2.9m(4H); 2.2s(3H); 1.3t(3H); 1.0d(6H) |
| 148 | 1 | H | H | CH₂—C≡CH | CH₂—CH₂—C₆H₄—4-CH₃ | 7.3-6.5m(7H); 4.7-4.0m(5H); 3.5-2.9m(3H); 4.0m(3H); 2.8-2.3m(4H); 2.2s(3H); 1.9-1.4m(3H) |

| | | | | | | |
|---|---|---|---|---|---|---|
| 149 | 1 | H | H | CH₂—CH—CH₃ <br> \|<br> CH₃ | CH₃ | CH₂—CH₂—CH(CH₃)₂ | 6.8–6.4m(3H); 4.7–4.3m(3H); 3.8–2.9m(4H); 4.0m(3H); 2.8–2.3m(2H); 1.9–1.4m(6H); 1.0d(15H) |
| 150 | 1 | H | H | ▷ (cyclopropyl) | H | CH₂—CH₂—C₆H₄—4-Cl | 7.3–6.5m(7H); 4.7–4.3m(3H); 3.8–2.9m(4H); 4.0s(3H); 2.8–2.3m(4H); 1.9–1.4m(2H); 1.1–0.6m(4H) |
| 151 | 1 | H | H | C₂H₅ | H | CH₂-indol-3-yl | 8.0s(1H); 7.6–6.5m(8H); 4.7–4.3m(3H); 3.8–2.9m(5H); 4.0s(3H); 2.8–2.3m(4H); 1.2t(3H) |
| 152 | 1 | H | C₂H₅ | C₂H₅ | H | CH₂CH₂—C(Cl)=C(CH₃)—N(C₆H₅)—N= (pyrazole deriv.) | 7.3–6.5m(8H); 4.7–4.3m(3H); 4.2q(2H); 4.0s(3H); 3.8–2.9m(5H); 2.8–2.3m(4H); 2.2s(3H); 1.9–1.4m(2H); 1.3t(3H); 1.1t(3H) |
| 153 | 1 | H | H | CH(CH₃)₂ | H | CH₂-benzothiophen-2-yl | 7.3–6.5m(8H); 4.7–4.3m(3H); 4.0s(3H); 4.0–2.9m(4H); 2.8–2.3m(4H); 1.1d(6H) |
| 154 | 1 | H | C₂H₅ | CH₃ | H | CH₂CH₂SC₆H₅ | 7.3–6.5m(8H); 4.7–4.3m(3H); 4.2q(2H); 1.0s(3H); 3.7–2.7m(5H); 2.7–2.3m(2H); 2.3s(3H); 1.9–1.4m(2H); 1.3t(2H) |
| 155 | 1 | H | H | CH₃ | H | CH₂—NHCOC₆H₅ | 7.8–6.5m(8H); 4.7–1.3m(3H); 4.0s(3H); 3.5–2.8m(5H); 2.7–2.3m(2H); 2.4s(3H) |
| 156 | 1 | H | H | decalinyl | H | CH₂CH₂—C₆H₅ | 7.2s(5H); 4.7–4.3m(1H); 3.5–2.9m(5H); 2.8–2.4m(2H); 2.3s(3H); 1.9–1.3m(14H) |
| 157 | 1 | H | C₂H₅ | CH₃ | H | CH₂CH₂—C₆H₅ | 7.2s(5H); 4.7–4.3m(1H); 4.2q(2H); 3.5–2.9m(5H); 2.8–2.4m(2H); 2.3s(3H); 1.9–1.3m(14H); 1.2t(3H) |
| 158 | 1 | H | H | C₂H₅ | H | CH₂CH₂—C₆H₄—4-F | 7.3–6.9m(4H); 4.7–4.3m(1H); 3.8–2.9m(7H); 2.8–2.4m(2H); 1.9–1.3m(14H); 1.1t(3H) |
| 159 | 1 | H | C₂H₅ | C₂H₅ | H | CH₂CH₂—C₆H₄—4-F | 7.3–6.9m(4H); 4.7–4.3m(1H); 4.2q(2H); 3.8–2.9m(7H); 2.8–2.4m(2H); 1.9–1.3m(14H); 1.3t(3H); 1.1t(3H) |

| | | | | | NMR |
|---|---|---|---|---|---|
| 160 | 1 | H | " | C₂H₅ | CH₂—CH₂—C₆H₄—4-OCH₃ | 6.9-6.4m(4H); 4.7-4.3m(1H); 3.8-2.9m(7H); 4.0s(3H); 2.8-2.4m(2H); 1.9-1.3m(14H); 1.1t(3H) |
| 161 | 1 | H | C₂H₅ | C₂H₅ | CH₂—CH₂—C₆H₄—4-OCH₃ | 6.9-6.4m(4H); 4.7-4.3m(1H); 4.2q(2H); 4.0s(3H); 3.8-2.9m(7H); 2.8-2.4m(2H); 1.9-1.3m(14H); 1.3t(3H); 1.1t(3H) |
| 162 | 1 | H | " | CH(CH₃)₂ | CH₂—CH₂—C₆H₄—2-CH₃ | 7.2s(4H); 4.7-4.3m(1H); 3.9-2.9m(6H); 2.8-2.4m(2H); 2.2s(3H); 1.9-1.3m(14H); 1.0d(6H) |
| 163 | 1 | H | C₂H₅ | CH(CH₃)₂ | CH₂—CH₂—C₆H₄—2-CH₃ | 7.2s(4H); 4.7-4.3m(1H); 4.2q(2H); 3.9-2.9m(6H); 2.8-2.4m(2H); 2.2s(3H); 1.9-1.3m(14H); 1.2t(3H); 1.0d(6H) |
| 164 | 1 | H | " | CH₂—CH=CH₂ | 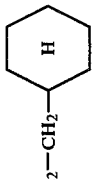 CH₂—CH₂—⟨cyclohexyl-H⟩ | 5.8m(1H); 5.0-4.2m(5H); 3.9-2.8m(5H); 1.9-1.2m(27H) |
| 165 | 1 | H | " | CH₃ | C₂H₅ | 4.7-4.3m(1H); 3.5-2.9m(5H); 2.4s(3H); 1.9-1.3m(14H); 0.9t(3H) |
| 166 | 1 | H | " | ⟨cyclobutyl⟩ | CH₂SOC₆H₅ | 7.2-6.8m(5H); 4.7-4.3m(1H); 3.8-2.9m(8H); 1.9-1.3m(18H) |
| 167 | 1 | H | " | C₂H₅ | CH₂NHCOC₆H₅ | 7.7-7.1m(5H); 4.7-4.3m(1H); 3.8-2.9m(8H); 1.9-1.3m(12H); 1.0d + t(6H) |
| 168 | 1 | H | C₂H₅ | n-C₃H₇ | CH₂—CH₂—C₆H₃—2-NO₂-4-NHCOCH₃ | 8.1-7.4m(3H); 4.7-4.3m(1H); 4.2q(2H); 3.8-2.9m(7H); 2.9-2.4m(2H); 1.9-1.3m(16H); 2.3s(3H); 1.3t(3H); 0.9t(3H) |
| 169 | 1 | H | " | CH₃ | 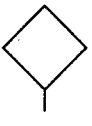 CH₂CH₂—⟨N-methylimidazole⟩ | 7.5-6.7m(2H); 4.7-4.3m(1H); 3.9-2.9m(4H); 3.7s(3H); 2.8-2.4m(2H); 1.9-1.4m(14H); 2.3s(3H); 1.0d(3H) |
| 170 | 1 | H | " | C₂H₅ | CH₂C₆H₄—C₆H₅ | 7.4-7.0m(9H); 4.7-4.3m(1H); 4.2q(2H); 3.8-2.9m(7H); 2.8-2.4m(2H); 1.9-1.4m(12H); 1.3t(3H); 1.0t(3H) |
| 171 | 1 | H | " | CH₃ | CH₂—CH₂—C₆H₃—(OCH₃)₂—2.5 | 6.9-6.2m(3H); 4.7-4.3m(1H); 4.0s(6H); 3.8-2.9m(4H); 2.8-2.4m(2H); 2.3s(3H); 1.9-1.4m(14H); 1.0d(3H) |

4,624,962

-continued

| No. | | | | | | NMR |
|---|---|---|---|---|---|---|
| 172 | 1 | H | H | C₂H₅ | (indole-CH₂-, N-H structure) | 8.0s(1H); 7.6-6.8m(5H); 4.7-4.3m(1H); 3.8-2.9m(7H); 2.8-2.4m(2H); 1.9-1.4m(12H); 1.1t(3H) |
| 173 | 1 | H | " | C₂H₅ | —CH₂—SO₂—C₆H₅ | 7.6-7.0m(5H); 4.7-4.3m(1H); 3.8-2.7m(8H); 1.9-1.4m(12H); 1.0-0.6m(4H) |
| 174 | 0 | H | " | CH₃ | (cyclopropyl) | H ; CH₂CH₂C₆H₆ ; 7.2s(5H); 4.7-4.3m(2H); 3.8-2.9m(2H); 2.8-2.4m(2H); 1.9-1.4m(14H); 2.4s(3H) |
| 175 | 0 | H | C₂H₅ | CH₃ | — | CH₂CH₂C₆H₅ ; 7.2s(5H); 4.7-4.3m(2H); 3.8-2.9m(2H); 2.8-2.4m(2H); 1.9-1.4m(14H); 2.4s(3H); 1.3t(3H) |
| 176 | 0 | H | " | C₂H₅ | — | CH₂CH₂C₆H₄—4-F ; 7.4-6.9m(4H); 4.7-4.3m(2H); 3.8-2.9m(4H); 2.8-2.4m(2H); 1.9-1.4m(14H); 1.0t(3H) |
| 177 | 0 | H | C₂H₅ | CH(CH₃)₂ | — | (CH₂CH₂-thiophene) ; 7.4-6.8m(3H); 4.7-4.3m(2H); 3.9-3.0m(3H); 4.2q(2H); 2.8-2.4m(2H); 1.9-1.4m(14H); 1.3t(3H); 1.0d(6H) |
| 178 | 0 | H | " | CH₂—CH=CH₂ | — | CH₂CH₂—C₆H₃(OCH₃)₂—3,4 ; 6.9-6.2m(3H); 5.8m(1H); 4.9-4.1m(6H); 3.7-3.0m(2H); 4.0s(6H); 2.8-2.4m(2H); 1.9-1.4m(14H) |
| 179 | 0 | H | C₂H₅ | (cyclopentyl) | — | CH₂—CH₂—C₆H₄—2-CH₃ ; 7.2s(4H); 4.7-4.3m(1H); 4.2q(2H); 3.8-2.9m(3H); 2.8-2.4m(2H); 2.2s(3H); 1.9-1.4m(22H); 1.3t(3H) |
| 180 | 0 | H | " | n-C₃H₇ | — | CH₂—CH₂—C₆H₃—2,6-Cl₂ ; 7.4-6.9m(3H); 4.7-4.3m(1H); 3.8-2.9m(4H); 2.8-2.4m(2H); 1.9-1.4m(16H); 1.0t(3H) |
| 181 | 1 | H | " | CH₃ | (2-ethyl-methylphenyl) | H ; CH₂—CH₂—C₆H₅ ; 7.2-6.5m(9H); 4.9t(1H); 3.8-3.0m(3H); 2.9-2.4m(4H); 2.4s(3H); 1.9-1.4m(2H); 1.2t(3H) |
| 182 | 1 | H | C₂H₅ | CH₃ | — | H ; CH₂—CH₂—C₆H₅ ; 7.2-6.5m(9H); 4.9t(1H); 4.2q(2H); 3.8-3.0m(3H); 2.9-2.4m(4H); 2.4s(3H); 1.9-1.4m(2H); 1.2t(3H) |
| 183 | 1 | H | " | C₂H₅ | — | H ; CH₂—CH₂—C₆H₄—4-F ; 7.2-6.5m(8H); 4.9t(1H); 3.8-3.0m(5H); 2.9-2.4m(4H); 1.9-1.4m(2H); 1.2t(3H) |

Structure:
$$R^2-N(R^3)(COOR^1)-C(=O)-N(R^4)-(CHR^5)_n-CH(R^6)(COOR^{1'})$$

| | n | R¹ | R¹' | R²-R³ | R⁴ | R⁵ | R⁶ | NMR |
|---|---|---|---|---|---|---|---|---|
| 184 | 1 | H | C₂H₅ | " | C₂H₅ | H | CH₂—CH₂—C₆H₄—4-F | 7.2-6.5m(8H); 4.9t(1H); 3.8-3.0m (5H); 4.2q(2H); 2.9-2.4m(4H); 1.9-1.4m(2H); 1.2t(3H); 1.0t(3H) |
| 185 | 1 | H | H | " | C₂H₅ | H | CH₂—CH₂—C₆H₅ | 7.2-6.5m(9H); 4.9t(1H); 3.8-3.0m (5H); 2.9-2.4m(4H); 1.9-1.4m(2H); 1.1t(3H) |
| 186 | 1 | H | C₂H₅ | 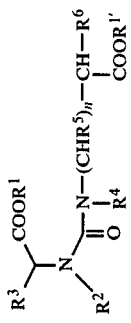 | C₂H₅ | H | CH₂—CH₂C₆H₅ | 7.2-6.5m(9H); 4.9t(1H); 3.8-3.0m(5H); 4.2q (2H); 2.9-2.4m(4H); 1.9-1.4m(2H); 1.3t(3H); 1.1t(3H) |
| 187 | 1 | H | H | " | C₂H₅ | H | CH₂—CH₂—C₆H₄—OCH₃—4 | 7.2-6.4m(8H); 4.9t(1H); 3.8-3.0m (5H); 2.9-2.4m(4H); 4.0s(3H)3.8-3.0m 1.1t(3H) |
| 188 | 1 | H | C₂H₅ | " | C₂H₅ | H | CH₂—CH₂—C₆H₄—OCH₃—4 | 7.2-6.4m(8H); 4.9t(1H); 4.2q(2H) 4.0s(3H); 3.8-3.0m(5H); 2.9-2.4m(4H); 1.9-1.4m(2H); 1.3t(3H); 1.1t(3H) |
| 189 | 1 | H | H | " | CH(CH₃)₂ | H | CH₂—CH₂—C₆H₄—2-CH₃ | 7.2-6.5m(8H); 4.9t(1H); 3.8-3.0m(4H); 2.9-2.4m(4H); 2.2s(3H); 1.9-1.4m(2H); 1.0d(6H) |
| 190 | 1 | H | C₂H₅ | " | CH(CH₃)₂ | H | CH₂—CH₂—C₆H₄—2-Cl₃ | 7.2-6.5m(8H); 4.9t(1H); 3.8-3.0m(4H); 2.2s(3H); 4.0q(2H); 1.9-1.4m(2H); 1.2t(3H); 1.0d(6H) |
| 191 | 1 | H | H | " | CH₂—C≡CH | H | CH₂—CH₂—CH₃ | 7.2-6.5m(4H); 4.9t(1H); 3.8-3.0m(5H); 2.9-2.6m(2H); 1.0t(3H) |
| 192 | 1 | H | C₂H₅ | " | CH₂—CH=CH₂ | CH₃ | CH₂—CH₂—CH(CH₃)₂ | 7.2-6.5m(4H); 5.8m(1H); 5.0-4.2m(5H); 3.8-3.0m(3H); 2.9-2.6m(2H); 4.2q(2H);1.9-1.4m(5H); 1.2t(3H); 1.0d(6H) |
| 193 | 1 | H | H | 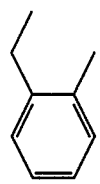 | 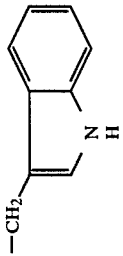 | H | CH₂SC₆H₅ | 7.3-6.5m(9H); 3.5-3.0m(4H); 2.9-2.4m(4H); 1.0-0.6m(4H) |
| 194 | 1 | H | C₂H₅ | " | CH(CH₃)₂ | H | CH₂CH₂OC₆H₅ | 7.2-6.5m(9H); 4.9t(1H); 4.2q(2H) 3.9-3.0m(6H); 3.0-2.6m(2H); 1.9-1.4m(2H); 1.2t(3H); 1.0d(6H) |
| 195 | 1 | H | H | " | CH₃ | H | —CH₂— (indol-3-ylmethyl) | 8.0s(1H); 7.5-6.5m(9H); 4.9t(1H); 4.0-3.0m(3H); 3.0-2.6m(4H); 2.4s(3H) |

| | | | | | |
|---|---|---|---|---|---|
| 196 | 1 | H | C₂H₅ | " | —CH₂-[indole] | H | C₂H₅ | 8.0s(1H); 7.5–6.5m(9H); 4.9t(1H) 4.2q(2H); 3.9–2.9m(5H); 3.0–2.6m(4H); 1.1t(3H) |
| 197 | 1 | H | " | CH₂-[pyridine] | H | C₂H₅ | 8.6–6.5m(8H); 4.9t(1H); 3.9–2.9m(5H); 2.9–2.5m(4H);1.9–1.4(2H); 1.1t(3H) |
| 198 | 1 | H | " | CH₂CH₂C₆H₅ | H | C₂H₅ | 7.2–6.5m(9H); 4.9t(1H); 3.9–2.9m(5H); 2.9–2.5m(4H); 1.9–1.4m(4H); 1.1t(3H) |
| 199 | 1 | H | " | CH₂C₆H₅ | H | C₂H₅ | 7.2–6.5m(9H); 4.9t(1H); 3.9–2.9m(5H); 2.9–2.5m(4H); 1.1t(3H) |
| 200 | 1 | H | " | CH₂CH₂C₆H₅ | CH₃ | CH(CH₃)₂ | 7.2–6.5m(9H); 4.9t(1H); 3.9–2.9m(3H); 2.9–2.5m(4H); 1.9–1.4m(2H); 1.0d+t(9H) |
| 201 | 0 | H | C₂H₅ | " | CH₂CH₂C₆H₅ | — | CH₃ | 7.2–6.5m(9H); 4.9–4.4m(2H); 4.2q(2H); 2.9–2.5m(4H); 2.4s(3H); 1.9–1.4m(2H); 1.2t(3H) |
| 202 | 0 | H | " | CH₂CH₂C₆H₅ | — | CH₃ | 7.2–6.5m(9H); 4.9–4.4m(2H); 2.9–2.5m(4H); 1.9–1.4m(2H) |
| 203 | 0 | H | C₂H₅ | " | CH₂CH₂C₆H₅ | — | C₂H₅ | 7.2–6.5m(9H); 4.9–4.4m(2H); 3.8–3.1m(2H); 4.2q(2H); 2.9–2.5m(4H); 1.9–1.4m(2H); 1.2t(3H) |
| 204 | 0 | H | " | CH₂–CH₂–C₆H₄–4-F | — | C₂H₅ | 7.2–6.5m(8H); 4.9–4.4m(2H); 3.8–3.1m(2H); 2.9–2.5m(4H); 1.9–1.4m(2H); 1.0t(3H) |
| 205 | 0 | H | C₂H₅ | " | CH₂–CH₂–C₆H₄–4-OCH₃ | — | CH(CH₃)₂ | 7.2–6.3m(8H); 4.9–4.4m(2H); 4.0–3.6m(1H); 4.2q(2H); 4.0s(3H); 2.9–2.5m(4H); 1.9–1.4m(2H); 1.2t(3H); 1.0d(6H) |
| 206 | 0 | H | " | CH₂CH₂C₆H₄–4-OCH₃ | — | CH(CH₃)₂ | 7.2–6.3m(8H); 4.9–4.4m(2H); 4.0s(3H); 1.9–1.4m(1H); 1.0d(6H) |
| 207 | 0 | H | " | CH₂CH₂–C₆H₃(OCH₂O)–3,4 | — | CH₂–CH=CH₂ | 7.2–6.2m(7H); 5.8m(1H); 5.0s(2H) 4.9–4.0m (6H); 2.9–2.5m(2H); 1.9–1.4m(2H) |
| 208 | 1 | H | " | CH₂–CH₂–C₆H₅ | H | C₂H₅ | 7.2s(5H); 4.8–4.4m(1H); 3.9–3.0m(8H); 3.2s(3H); 2.9–2.5m(2H); 1.9–1.4m(12H); 1.1t(3H) |
| 209 | 1 | H | C₂H₅ | [decalin-OCH₃] | CH₂–CH₂–C₆H₅ | H | C₂H₅ | 7.2s(5H); 4.8–4.4m(1H); 4.2q(2H); 3.2s(3H); 3.9–3.0m(8H); 2.9–2.5m(2H); 1.9–1.4m(12H); 1.3(3H) |
| 210 | 1 | H | " | CH₂–CH₂–C₆H₄–4-F | H | CH₃ | 7.4–6.9m(4H); 2.9–2.5m(2H) 2.3s(3H); 1.9–1.4m(12H); 3.9–3.0m(6H); 3.2s(3H); 4.2q(2H); 2.9–2.5m(2H); 2.3s(3H); 1.9–1.4m(12H); 1.2t(3H) |
| 211 | 1 | C₂H₅ | " | CH₂–CH₂–C₆H₄–4-F | H | CH₃ | 7.4–6.9m(4H); 4.7–4.4m(1H); 3.9–3.0m(6H); 3.2s(3H); 4.2q(2H); 2.9–2.5m(2H); 2.3s(3H); 1.9–1.4m(12H); 1.2t(3H) |
| 212 | 1 | H | " | CH₂–CH₂–C₆H₄–2-OCH₃ | H | C₂H₅ | 7.0–6.5m(4H); 4.7–4.4m(1H); 3.9s(3H); |

-continued

| No. | n | | | | | NMR |
|---|---|---|---|---|---|---|
| 213 | 1 | C₂H₅ | H | CH(CH₃)₂ | CH₂—CH₂—C₆H₃—2,6-Cl₂ | 3.9-3.0m(8H); 3.2s(3H); 2.9-2.5m(2H); 1.9-1.4m(12H); 1.0t(3H) |
| 214 | 1 | H | H | CH(CH₃)₂ | CH₂NHCOC₆H₅ | 7.2-6.9m(3H); 4.2q(2H); 3.2s(3H); 4.0-3.1m(7H); 1.9-1.4m(12H); 1.2t(3H); 1.0d(6H) |
| 215 | 1 | C₂H₅ | H | CH(CH₃)₂ | CH₂NHCOCH₃ | 7.8-7.3m(5H); 4.7-4.4m(1H); 3.9-3.0m(9H); 3.2s(3H); 1.9-1.4m(10H); 1.0d(6H) |
| 216 | 1 | C₂H₅ | H | C₂H₅ | cyclohexyl-CH₂ | 4.7-4.4m(1H); 4.0-3.0m(9H); 3.2s(3H); 2.4s(3H); 1.9-1.4m(10H); 4.2q(2H); 1.2t(3H); 1.0d(6H) |
| 217 | 1 | H | H | CH₂—CH=CH₂ | indol-3-yl-CH₂ | 4.7-4.4m(1H); 4.2q(2H); 3.8-3.0m(8H); 3.2s(3H); 1.9-1.4m(23H); 1.2t(3H); 1.0t(3H) |
| 218 | 1 | H | H | cyclobutyl (with 3-methoxy-4-methyl-5-ethylphenyl group shown) | CH₂SOC₆H₅ | 8.0s(1H); 7.6-6.6m(5H); 5.8m(1H); 5.0m(5H); 4.7-4.4m(1H); 3.9-3.0m(6H); 2.9-2.4m(2H); 3.2s(3H); 1.9-1.4m(10H) |
| 219 | 1 | H | H | —CH₂—C≡CH | CH₂NHC₆H₅ | 7.6-7.0m(5H); 4.7-4.4m(1H); 3.9-2.9m(9H); 3.2s(3H); 1.9-1.4m(16H) |
| 220 | 1 | C₂H₅ | H | CH₂—C≡C—CH₃ | CH₂CH₂C₆H₅ | 7.2-6.5m(5H); 4.7-4.0m(3H); 3.8-2.9m(6H); 2.9-2.6m(2H); 3.2s(3H); 1.9-1.4m(11H) |
| 221 | 1 | H | H | C₂H₅ | CH₂CH₂C₆H₅ | 7.2s(5H); 4.7-4.0m(3H); 4.2q(2H); 3.8-2.9m(6H); 3.2s(3H); 2.9-2.4m(2H); 1.9-1.3m+s(17H); 1.2t(3H) |
| 222 | 1 | C₂H₅ | H | C₂H₅ | CH₂CH₂C₆H₅ | 7.2-6.3m(8H); 4.9t(1H); 3.9s(3H); 3.9-3.0m(5H); 2.9-2.4m(4H); 1.9-1.4m(2H); 1.1t(3H) |
| 223 | 1 | H | H | CH(CH₃)₂ | CH₂CH₂C₆H₄—4-F | 7.2-6.3m(8H); 4.9t(1H); 4.2q(2H) 3.9s(3H); 3.9-3.0m(5H); 2.9-2.4m(4H); 1.9-1.4m(3H); 1.0t(3H) |
| 224 | 1 | C₂H₅ | H | CH(CH₃)₂ | CH₂CH₂—C₆H₄—4-F | 7.2-6.3m(7H); 4.9t(1H); 4.2q(2H); 3.9s(3H); 3.9-3.0m(4H); 2.9-2.4m(4H); 1.9-1.4m(2H); 1.3t(3H); 1.0d(6H) |

| | | | | | -continued | |
|---|---|---|---|---|---|---|
| 225 | 1 | H | " | CH₃ | CH₃ | 7.3-6.5m(6H); 4.9t(1H); 3.9s(3H); 3.9-3.0m(2H); 2.4s(3H); 2.9-2.4m(4H); 1.9-1.4m(2H); 1.0d(3H) |
| 226 | 1 | H | " | C₂H₅ | CH₂CH₂- | 7.3-6.3m(6H); 4.9t(1H); 3.9s(3H) 3.9-3.0m(5H); 2.9-2.4m(4H); 1.9-1.4m(2H); 1.2t(3H) |
| 227 | 1 | H | " | CH₂CH₂CH₃ | CH₂—CH₂—C₆H₃—2.6-Cl₂ | 7.2-6.3m(7H); 4.9t(1H); 3.9s(3H) 3.9-3.0m(5H); 2.9-2.4m(4H); 2.2s(3H); 1.9-1.4m(4H); 1.0t(3H) |
| 228 | 1 | H | " | CH₂—CH=CH₂ | CH₂—CH₂—C₆H₄—2-CH₃ | 7.4-6.1m(6H); 5.8m(1H); 5.0-4.3m(5H); 3.9s(9H); 3.9-3.0m(3H); 2.9-2.4m(4H); 1.9-1.4m(2H) |
| 229 | 1 | C₂H₅ | " | 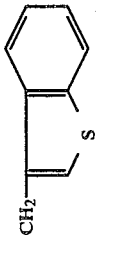 | CH₂—CH₂—C₆H₃—(OCH₃)₂-3.4 | 8.2-6.4m(7H); 4.9t(1H); 4.2q(2H) 3.9s(3H); 3.9-3.0m(4H); 2.9-2.4m(4H); 1.9-1.2m(8H); 1.2t(3H) |
| 230 | 1 | H | " | C₂H₅ | CH₂CH₂—C₆H₄—2-Cl—4-NO₂ | 7.4-6.3m(8H); 4.9t(1H); 3.9s(3H) 3.9-3.0m(5H); 2.9-2.4m(4H); 1.1t(3H) |
| 231 | 1 | H | " | C₂H₅ | CH₂—CH₂—CH(CH₃)₂ | 7.3-6.4m(8H); 4.9t(1H); 3.9s(3H) 3.9s(3H); 3.9-3.0m(4H); 2.9-2.6m(2H); 1.9-1.4m(2H); 1.2t(3H); 1.0d+t(9H) |
| 232 | 1 | C₂H₅ | " | CH(CH₃)₂ | CH₂H₃ | 7.3-6.4m(3H); 4.9t(1H); 4.2q(2H); 3.9s(3H); 3.9-3.0m(4H); 2.9-2.6m(2H); 1.9-1.4m(2H); 1.2t(3H); 1.0d+t(6H) |
| 233 | 1 | C₂H₅ | " | C₂H₅ | CH₂CH₂SC₆H₅ | 7.3-6.4m(8H); 4.9t(1H); 4.2q(2H); 3.9s(3H); 3.9-3.0m(5H); 2.9-2.6m(2H); 1.9-1.4m(2H);1.2t(3H); 1.0t(3H) |
| 234 | 1 | H | " | CH₂CH₂CH₃ | CH₂CH₂NHCOC₆H₅ | 7.6-6.4m(8H); 4.9t(1H); 3.9s(3H) 3.9-3.0m(6H); 3.0-2.7m(2H); 1.9-1.4m(6H); 1.0d+t(6H) |
| 235 | 1 | C₂H₅ | " | CH₃ | n-C₆H₁₃ | 7.3-6.5m(3H); 4.9t(1H); 4.2q(2H); 3.9s (3H); 3.9-3.0m(2H); 2.9-2.6m(2H); 2.4s(3H); 1.9-1.4m(10H); 1.2t(3H); 1.0d+t(6H) |
| 236 | 1 | H | " | C₂H₅ | CH₂CH₂C₆H₅ | 7.2-6.4m(8H); 4.9-4.4m(2H); 3.9s (3H); 3.9-3.0m(2H); 3.0-2.6m(4H); 1.9-1.4m(2H); 1.0t(3H) |
| 237 | 0 | C₂H₅ | " | CH(CH₃)₂ | CH₂—CH₂—C₆H₄—4-F | 7.3-6.4m(7H); 4.9-4.4m(2H); 3.9s(3H); 4.2q(2H); 4.0-3.6m(1H); 3.0-2.6m(4H); 1.9-1.4m(2H); 1.2t(3H); 1.0d(6H) |
| 238 | 0 | H | " | CH₂—CH=CH₂ | CH₂CH₂—C₆H₄—4-OCH₃ | 7.3-6.2m(7H); 5.8m(1H); 5.0-4.2m(6H); 3.9s(6H); 3.0-2.6m(4H); 1.9-1.4m(2H) |
| 239 | 0 | H | " | CH(CH₃)₂ | CH₂CH₂- | 7.3-6.4m(6H); 4.9-4.4m(2H); 3.9s(3H); 3.9-3.5m(1H); 3.0-2.6m(4H); 1.4m(2H); 1.1d(6H) |

4,624,962

-continued

| | | | | | NMR |
|---|---|---|---|---|---|
| 240 | 0 | H | $C_2H_5$ | " | — | $CH_2CH_2-C_6H_3(OCH_3)_2-2.5$ | 7.3-6.2m(6H); 4.9-4.4m(2H); 3.9s(9H); 3.9-3.5m(1H); 3.0-2.6m(4H); 1.9-1.4m(8H); 4.2q(2H); 1.2t(3H) |
| 241 | 1 | H | H | " | $CH_3$ | $CH_2CH_2C_6H_5$ | 7.2s(5H); 4.8-4.4m(1H); 3.9-3.0m(4H); 2.9-2.6m(2H); 2.3s(3H); 1.9-1.4m(13H); 1.2t(3H) |
| 242 | 1 | H | $C_2H_5$ | " | $CH_3$ | $CH_2CH_2C_6H_5$ | 7.2s(5H); 4.8-4.4m(1H); 4.2q(2H) 3.9-3.0m(4H); 2.9-2.6m(2H); 2.3s (3H); 1.9-1.4m(13H); 1.2t(3H) |
| 243 | 1 | H | H | " | $C_2H_5$ | $CH_2CH_2C_6H_4-4-F$ | 7.3-6.9m(4H); 4.8-4.4m(1H); 3.9-3.0m (6H); 2.9-2.6m(2H); 1.9-1.4m(13H); 1.0t(3H) |
| 244 | 1 | H | $C_2H_5$ | " | $C_2H_5$ | $CH_2CH_2C_6H_4-4-F$ | 7.3-6.9m(4H); 4.8-4.4m(1H); 4.2q(2H); 3.9-3.0m(6H); 2.9-2.6m(2H); 1.9-1.4m (13H); 1.2t(3H); 1.0t(3H) |
| 245 | 1 | H | H | " | $CH(CH_3)_2$ | $CH_2CH_2C_6H_4-4-F$ | 7.3-6.9m(4H); 4.8-4.4m(1H); 3.9-3.0m(5H); 2.9-2.6m(2H); 1.9-1.4m(13H); 1.0d(6H) |
| 246 | 1 | H | $C_2H_5$ | 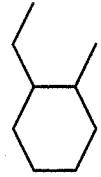 | $CH(CH_3)_2$ | $CH_2-CH_2-C_6H_4-4-F$ | 7.3-6.9m(4H); 4.8-4.4m(1H); 4.2q(2H); 3.9-3.0m(5H); 2.9-2.6m(2H); 1.9-1.4m(13H); 1.2t(3H); 1.0d(6H) |
| 247 | 1 | H | H | " | $CH_2-CH=CH_2$ | $CH_2-CH_2-C_6H_4-4-OCH_3$ | 7.0-6.3m(4H); 5.8m(1H); 5.0-4.2m(5H); 3.9-3.0m(4H); 3.9s(3H); 2.9-2.6m(2H); 1.9-1.4m(13H) |
| 248 | 1 | H | $C_2H_5$ | " | $CH_2-CH=CH_2$ | $CH_2-CH_2-C_6H_4-4-OCH_3$ | 7.0-6.3m(4H); 5.8m(1H); 5.0-4.2m(5H); 4.2q(2H); 3.9-3.0m(4H); 3.9s(3H); 2.9-2.6m(2H); 1.9-1.4m(13H); 1.2t(3H) |
| 249 | 1 | H | H | " | $C_2H_5$ | $CH_2-CH_2-C_6H_4-4-OCH_3$ | 7.0-6.3m(4H); 4.8-4.4m(1H); 3.9-3.0m(6H); 2.9-2.4m (4H); 1.9-1.4m(13H); 1.0t(3H) |
| 250 | 1 | H | $C_2H_5$ | " | $C_2H_5$ | $CH_2-CH_2-C_6H_4-4-OCH_3$ | 7.0-6.3m(4H); 4.8-4.4m(1H); 4.2q(2H); 3.9-3.0m(6H); 2.9-2.4m(4H); 1.9-1.4m(13H); 1.2t(2H); 1.0t(3H) |
| 251 | 1 | H | H | " | $C_2H_5$ | $CH_2-CH_2-C_6H_4-2-CH_3$ | 7.2s(4H); 4.8-4.4m(1H); 3.9-3.0m(6H); 2.9-2.4m(4H); 2.1s(3H); 1.9-1.4m(13H); 1.0t(3H) |
| 252 | 1 | H | $C_2H_5$ | " | $C_2H_5$ | $CH_2-CH_2-C_6H_4-2-CH_3$ | 7.2s(4H); 4.8-4.4m(1H); 4.2q(2H) 3.9-3.0m(6H); 2.9-2.4m(4H); 2.1s(3H); 1.9-1.4m(13H); 1.2t(3H); 1.0t(3H) |
| 253 | 1 | H | H | " | $CH_2-C\equiv CH$ | $CH_2-CH_2-C_6H_4-2-CH_3$ | 7.2s(4H); 4.8-4.0m(3H); 3.9-3.0m(4H); 2.9-2.4m (4H); 2.1s(3H); 1.9-1.4m(14H); 1.0t(3H) |
| 254 | 1 | H | $C_2H_5$ | " | $CH_2-C\equiv CH$ | $CH_2-CH_2-C_6H_4-2-CH_3$ | 7.2s(4H); 4.8-4.0m(5H); 4.2q(2H) 3.9-3.0m(4H); 2.9-2.4m(4H); 2.1s(3H); 1.9-1.4m(14H); 1.2t(3H); 1.0t(3H) |
| 255 | 1 | H | H | " | $C_2H_5$ | $CH_2SC_6H_5$ | 7.2s(5H); 4.8-4.4m(4H); 3.9-3.0m(6H); 2.9-2.4m(4H); 1.9-1.4m(11H); 1.1t(3H) |
| 256 | 1 | H | $C_2H_5$ | " | $C_2H_5$ | $CH_2SOC_6H_5$ | 7.5-7.0m(5H); 4.8-4.4m(1H); 4.2q(2H); 3.9-3.0m(6H); 2.9-2.4m(4H); 1.9-1.4m(11H); 1.2t(3H); 1.0t(3H) |
| 257 | 1 | H | $C_2H_5$ | " | $C_2H_5$ | $CH_2SO_2C_6H_5$ | 7.5-7.0m(5H); 4.8-4.4m(1H); 4.2q(2H); 3.9-3.0m |

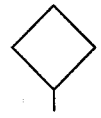

| | | | | |
|---|---|---|---|---|
| 258 | 1 | H | H | C₂H₅ | CH₂NHCOC₆H₅ | (6H); 2.9–2.4m(4H); 1.9–1.4m(11H); 1.2t(3H); 1.0t(3H) |
| 259 | 1 | H | H | C₂H₅ | CH₂NHC₆H₅ | 7.7–7.2m(5H); 4.7–4.4m(1H); 3.9–3.0m(8H); 2.9–2.4m(2H); 1.9–1.4m(11H); 1.0t(3H) |
| 260 | 1 | H | H | C₂H₅ |  CH₂CH₂—[thiophene] | 7.1–6.5m(5H); 4.7–4.4m(1H); 3.9–3.0m(6H); 2.9–2.4m(4H); 1.9–1.4m(13H); 1.0t(3H) |
| 261 | 1 | H | H | C₂H₅ | CH₂CH₂CH₃ | 7.2–6.8m(3H); 3.9–3.0m(6H); 2.9–2.4m(4H); 1.9–1.4m(13H); 1.0t(3H) |
| 262 | 1 | H | H | C₂H₅ | CH₂CH₂C₆H₃(OCH₃)₂—3,4 | 4.7–4.4m(1H); 3.9–3.0m(6H); 2.9–2.4m(2H); 1.9–1.4m(17H); 1.0t(6H) |
| 263 | 1 | H | H | C₂H₅ | CH₂OC₆H₅ | 6.9–6.2m(3H); 4.7–4.4m(1H); 3.9s(6H); 3.9–3.0m(6H); 2.9–2.4m((4H); 1.9–1.4m(13H); 1.0t(3H) |
| 264 | 1 | H | H | C₂H₅ | CH₂CH₂OC₆H₅ | 7.0–6.5m(5H); 4.7–4.4m(1H); 3.9–3.0m(8H); 2.4m(2H); 1.9–1.4m(11H); 1.0t(3H) |
| 265 | 1 | H | H | CH(CH₃)₂ | 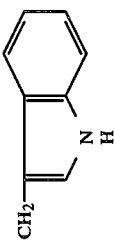 CH₂—[indole] | 7.0–6.5m(5H); 4.7–4.4m(1H); 3.9–3.0m(8H); 2.4m(2H); 1.9–1.4m(13H); 1.0t(3H) |
| | | | | | | 8.0s(1H); 7.6–6.8m(5H); 4.7–4.4m(1H); 3.9–3.0m (5H); 2.9–2.4m(4H); 1.9–1.4m(11H); 1.0d(6H) |
| 266 | 0 | H | H | C₂H₅ | CH₂CH₂C₆H₅ | 7.2s(5H); 4.8–4.3m(2H); 3.9–3.0m(3H); 2.9–2.4m(2H); 1.9–1.4m(13H); 1.0t(3H) |
| 267 | 0 | H | C₂H₅ | CH(CH₃)₂ | CH₂CH₂—C₆H₄—4-F | 7.2–6.8m(4H); 4.8–4.3m(2H); 4.2q(2H); 3.9–3.0m(2H); 2.9–2.4m(2H); 1.9–1.4m(13H); 1.2t(3H); 1.0d(6H) |
| 268 | 0 | H | H | CH₂—CH═CH₂ | CH₂—CH₂—C₆H₅—(OCH₂O)—3,4 | 6.9–6.2m(3H); 5.8m(1H); 5.0s(2H); 5.0–4.2m (6H); 3.9–3.4m(1H); 2.9–2.4m(2H); 1.9–1.4m(13H) |
| 269 | 0 | H | C₂H₅ | CH₂CH₂CH₃ | CH₂—CH₂—C₆H₄—OCH₃—4 | 7.0–6.4m(4H); 4.8–4.3m(2H); 4.2q(2H); 3.9–3.0m(3H); 3.9s(3H); 2.9–2.5m(2H); 1.9–1.4m(15H); 1.2t(3H); 1.0t(3H) |
| 270 | 0 | H | H | [cyclobutyl] | CH₂CH₂C₆H₄—2-CH₃ | 7.2s(4H); 4.8–4.3m(2H); 3.9–3.1m(2H); 2.9–2.5m(2H); 2.1s(3H); 1.9–1.4m(19H) |
| 271 | 1 | H | H | [cyclohexyl with CH₃O, ethyl, methyl substituents] | C₂H₅ | CH₂CH₂C₆H₅ | 7.2s(5H); 4.8–4.4m(1H); 3.9–3.0m(7H); 3.2s(3H); 2.9–2.4m(2H); 1.9–1.4m(12H); 1.0t(3H) |

| # | | | | | NMR |
|---|---|---|---|---|---|
| 272 | 1 | H | C₂H₅ | " | CH₂CH₂C₆H₅ | H | 7.2s(5H); 4.8–4.4m(1H); 4.2q(2H); 3.9–3.0m(7H); 3.2s(3H); 2.9–2.4m(2H); 1.9–1.4m(12H); 1.2t(3H); 1.0t(3H) |
| 273 | 1 | H | C₂H₅ | " | CH₂CH₂C₆H₅ | H | 7.2s(5H); 4.8–4.4m(1H); 4.2q(2H); 3.9–3.0m(5H); 3.2s(3H); 2.9–2.4m(2H); 2.3s(3H); 1.9–1.4m(12H); 1.2t(3H) |
| 274 | 1 | H | H | " | CH₂CH₂C₆H₅ | H | 7.2s(5H); 4.8–4.4m(1H); 3.9–3.0m(5H); 2.9–2.4m(2H); 2.3s(3H); 1.9–1.4m(12H) |
| 275 | 1 | H | H | " | CH₂CH₂—C₆H₄—4-F | H | 7.4–6.9m(4H); 4.8–4.4m(1H); 3.9–3.0m(7H); 3.2s(3H); 2.9–2.4m(2H); 1.9–1.4m(12H); 1.0t(3H) |
| 276 | 1 | H | C₂H₅ | " | CH₂CH₂—C₆H₄—4-F | H | 7.4–6.9m(4H); 4.8–4.4m(1H); 3.9–3.0m(7H); 4.2q(2H); 3.2s(3H); 2.9–2.4m(2H); 1.9–1.4m(12H); 1.2t(3H) |
| 277 | 1 | H | H | " | CH₂CH₂—C₆H₄—4-F | CH(CH₃)₂ | 7.4–6.9m(4H); 4.8–4.4m(1H); 3.9–3.0m(6H); 3.2s(3H); 2.9–2.4m(2H); 1.9–1.4m(12H); 1.0d(6H) |
| 278 | 1 | H | C₂H₅ | " | CH₂CH₂—C₆H₄—4-F | CH(CH₃)₂ | 7.4–6.9m(4H); 4.8–4.4m(1H); 3.9–3.0m(6H); 4.2q(2H); 3.2s(3H); 2.9–2.4m(2H); 1.9–1.4m(12H); 1.2t(3H); 1.0d(6H) |
| 279 | 1 | H | H | " | CH₂CH₂—C₆H₄—4-OCH₃ | CH₂—CH=CH₂ | 7.0–6.4m(4H); 5.8m(1H); 5.0–4.2m(5H); 4.2q(2H); 3.9s(3H); 3.9–3.0m(5H); 3.2s(3H); 2.9–2.4m(2H); 1.9–1.4m(12H); 1.2t(3H) |
| 280 | 1 | H | H | " | CH₂CH₂—C₆H₄—4-OCH₃ | CH₂—CH=CH₂ | 7.0–6.4m(4H); 5.8m(1H); 5.0–4.2m(5H); 3.9s(3H); 3.9–3.0m(5H); 3.2s(3H); 2.9–2.4m(2H); 1.9–1.4m(12H) |
| 281 | 1 | H | H | " | CH₂CH₂—C₆H₄—4-OCH₃ | CH₃ | 7.0–6.4m(4H); 4.8–4.4m(1H); 3.9–3.0m(6H); 3.9s(3H); 3.2s(3H); 2.9–2.4m(2H); 1.9–1.4m(12H); 1.0d+t(6H) |
| 282 | 1 | H | C₂H₅ | " | CH₂CH₂—C₆H₄—4-OCH₃ | CH₃ | 7.0–6.4m(4H); 4.8–4.4m(1H); 4.2q(2H); 3.9–3.0m(6H); 3.9s(3H); 3.2s(3H); 2.9–2.4m(2H); 1.9–1.4m(12H); 1.2t(3H); 1.0d+t(6H) |
| 283 | 1 | H | H | " | CH₂CH₂—C₆H₄—2-CH₃ | H | 7.2s(4H); 4.8–4.4m(1H); 3.9–3.0m(7H); 3.2s(3H); 2.9–2.4m(2H); 2.1s(3H); 1.9–1.4m(12H); 1.0t(3H) |
| 284 | 1 | H | C₂H₅ | " | CH₂CH₂—C₆H₄—2-CH₃ | H | 7.2s(4H); 4.8–4.4m(1H); 4.2q(2H); 3.9–3.0m(7H); 3.2s(3H); 2.9–2.4m(2H); 2.1s(3H); 1.9–1.4m(12H); 1.2t(3H); 1.0t(3H) |
| 285 | 1 | H | H | " | CH₂CH₂—C₆H₄—2-CH₃ | CH₂—C≡CH | 7.2s(4H); 4.8–4.4m(1H); 4.3–3.0m(7H); 3.2s(3H); 2.9–2.4m(2H); 2.1s(3H); 1.9–1.4m(13H) |
| 286 | 1 | H | C₂H₅ | " | CH₂CH₂—C₆H₄—2-CH₃ | CH₂—C≡CH | 7.2s(4H); 4.8–4.4m(1H); 4.3–3.0m(9H); 3.2s(3H); 2.9–2.4m(2H); 2.1s(3H); 1.9–1.4m(13H); 1.2t(3H) |
| 287 | 1 | H | H | " | CH₂SC₆H₅ | H | 7.2s(5H); 4.8–4.4m(1H); 3.9–3.0m(7H); 3.2s(3H); 2.9–2.4m(2H); 1.9–1.4m(10H); 1.0t(3H) |
| 288 | 1 | H | C₂H₅ | " | CH₂SOC₆H₅ | H | 7.4–7.0m(5H); 4.8–4.4m(1H); 4.2q(2H); 3.9–3.0m(7H); 3.2s(3H); 2.9–2.4m(2H); 1.9–1.4m(10H); 1.2t(3H); 1.0t(3H) |

| | n | R¹ | R¹' | R²–R³ | R⁴ | R⁵ | R⁶ | |
|---|---|---|---|---|---|---|---|---|
| 289 | 1 | H | C₂H₅ | CH₃O–[cyclohexyl with ethyl and methyl] | C₂H₅ | H | CH₂SO₂C₆H₅— | 7.6–7.0m(5H); 4.8–4.4m(1H); 4.2q(2H); 3.9–3.0m(7H); 3.2s(3H); 3.1–2.6m(2H); 1.9–1.4m(10H); 1.2t(3H); 1.0t(3H) |
| 290 | 1 | H | H | " | C₂H₅ | H | CH₂NHCOC₆H₅ | 7.9–7.3m(5H); 4.8–4.4m(1H); 3.9–2.8m(9H); 3.2s(3H); 1.9–1.4m(10H); 1.0t(3H) |
| 291 | 1 | H | H | " | C₂H₅ | H | CH₂NHC₆H₅ | 7.0–6.4m(5H); 4.8–4.4m(1H); 3.9–2.8m(9H); 3.2s(3H); 1.9–1.4m(12H); 1.0t(3H) |
| 292 | 1 | H | H | " | C₂H₅ | H |  CH₂CH₂—[thiophene] | 7.2–6.7m(3H); 4.8–4.4m(1H); 3.9–3.1m(7H); 3.2s(3H); 2.9–2.5m(2H) 1.9–1.4m(12H); 1.0t(3H) |
| 293 | 1 | H | H | " | C₂H₅ | H | CH₂CH₂CH₃ | 4.8–4.4m(1H); 3.9–3.1m(7H); 3.2s(3H); 1.9–1.4m(14H); 1.0t(6H) |
| 294 | 1 | H | H | " | C₂H₅ | CH₃ | CH₂CH₂—CH(CH₃)₂ | 4.8–4.4m(1H); 3.9–3.1m(6H); 3.2s(3H); 1.9–1.4m(15H); 1.0t+d(12H) |
| 295 | 1 | H | H | " | [cyclopentylmethyl] | H | CH₂CH₂—C₆H₃(OCH₃)₂—3.4 | 6.9–6.2m(3H); 3.9s(6H); 3.9–3.1m(6H); 3.2s(3H); 2.9–2.4m(2H); 1.9–1.4m(20H) |
| 296 | 1 | H | H | " | CH(CH₃)₂ | H | CH₂OC₆H₅ | 7.0–6.6m(5H); 3.9–3.1m(8H); 3.2s(3H); 1.9–1.4m(10H); 1.0d(6H) |
| 297 | 1 | H | H | " | C₂H₅ | H | CH₂CH₂OC₆H₅ | 7.1–6.6m(5H); 4.8–4.4m(1H); 3.9–3.1m(9H); 3.2s(3H); 2.0–1.3m(12H); 1.0t(3H) |
| 298 | 1 | H | H | " | CH₃ | H |  CH₂—[indole] | 8.0s(1H); 7.6–6.7m(5H); 4.8–4.4m(1H); 3.9–3.1m(5H); 3.2s(3H); 2.9–2.4m(2H); 2.3s(3H); 1.9–1.4m(10H) |
| 299 | 1 | H | H | " | CH(CH₃)₂ | H | 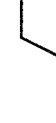 CH₂CH₂—[pyridine] | 8.6–7.4m(4H); 4.8–4.4m(1H); 3.9–3.1m(6H); 3.2s(3H); 2.9–2.4m(2H); 1.9–1.4m(12H); 1.0d(6H) |

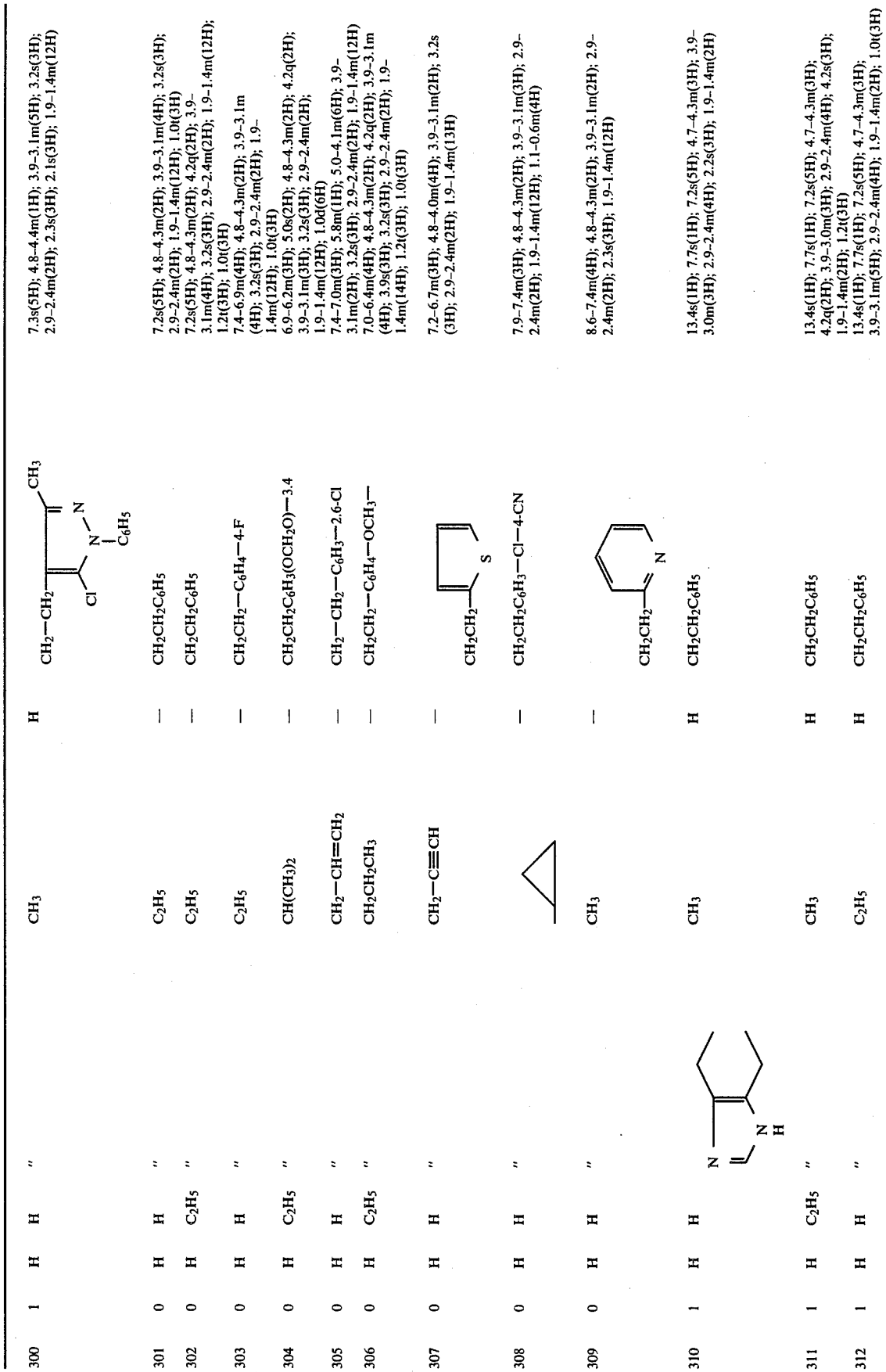

| | | | | | NMR data |
|---|---|---|---|---|---|
| 313 | 1 | H | C2H5 | H | CH2CH2C6H5 | 13.4s(1H); 7.7s(1H); 7.2s(5H); 4.7-4.3m(3H); 4.2q(2H); 3.9-3.1m(5H); 2.9-2.4m(4H); 1.9-1.4m(2H); 1.2t(3H); 1.0t(3H) |
| 314 | 1 | H | CH(CH3)2 | H | CH2CH2C6H5 | 13.4s(1H); 7.7s(1H); 7.2s(5H); 4.7-4.3m(3H); 3.9-3.1m(4H); 2.9-2.4m(4H); 1.9-1.4m(2H); 1.0d(6H) |
| 315 | 1 | H | CH(CH3)2 | C2H5 | CH2CH2C6H5 | 13.4s(1H); 7.7s(1H); 7.2s(5H); 4.7-4.3m(3H); 4.2q(2H); 3.9-3.0m(4H); 2.9-2.4m(4H); 1.9-1.4m(2H); 1.2t(3H); 1.0d(6H) |
| 316 | 1 | H | CH2CH2CH3 | H | CH2CH2C6H4—4-F | 13.4s(1H); 7.7s(1H); 7.4-6.9m(4H); 4.7-4.3m(3H); 3.9-3.0m(5H); 2.9-2.4m(4H); 1.9-1.4m(4H); 1.0t(3H) |
| 317 | 1 | H | CH2CH2CH2CH3 | H | CH2CH2C6H3—(OCH3)2—3,4 | 13.4s(1H); 7.7s(1H); 6.9-6.2m(3H); 4.7-4.3m(3H); 3.9-3.0m(5H); 3.9s(6H); 2.9-2.4m(4H); 1.9-1.4m(6H); 1.0t(3H) |
| 318 | 1 | H |  | H | CH2CH2CH2CH3 | 13.4s(1H); 7.7s(1H); 4.7-4.3m(3H); 3.9-3.0m (4H); 2.9-2.4m(2H); 1.9-1.4m(6H); 1.1-0.5t+m(7H) |
| 319 | 1 | H | CH2—C≡CH | H | CH2—S—C6H5 | 13.4s(1H); 7.2s(5H); 4.8-4.0m(5H); 3.9-3.0m(3H); 2.9-2.4m(4H); 1.8s(1H) |
| 320 | 1 | H | CH2—CH=CH2 | CH3 | CH2CH2—C6H4-4-OCH3 | 13.4s(1H); 7.7s(1H); 6.8-6.3m(4H); 5.8m(1H); 5.0-4.1m(7H); 3.9s(3H); 3.9-3.0m(2H); 2.9-2.4m(4H); 1.0d(3H) |
| 321 | 1 | H | C2H5 | H | CH2NH—COC6H5 | 13.4s(1H); 7.9-7.4m(6H); 4.7-4.3m(3H); 4.2q(2H); 3.9-3.1m(7H); 2.9-2.5m(2H); 1.3t(3H); 1.0t(3H) |
| 322 | 1 | H | C2H5 | H | CH2CH2OC6H5 | 13.4s(1H); 7.7s(1H); 7.1-6.6m(5H); 4.7-4.3m(3H); 3.9-3.1m(7H); 2.9-2.5m(2H); 1.9-1.4m(2H); 1.0t(3H) |
| 323 | 1 | H | CH3 | H |  | 7.3-6.9m(7H); 4.9-4.4m(3H); 3.9-3.1m(3H); 3.0-2.4m(4H); 2.3s(3H); 1.9-1.4m(2H) |
| 324 | 1 | H | CH3 | C2H5 | CH2CH2C6H5 | 7.3-6.9m(7H); 4.9-4.4m(3H); 4.2q(2H); 3.9-3.1m(5H); 3.0-2.4m(4H); 2.3s(3H); 1.9-1.4m(2H); 1.2t(3H) |
| 325 | 1 | H | C2H5 | H | CH2CH2C6H5 | 7.3-6.9m(7H); 4.9-4.4m(3H); 3.9-3.1m(3H); 3.0-2.4m(4H); 1.9-1.4m(2H); 1.0t(3H) |
| 326 | 1 | H | C2H5 | C2H5 | CH2CH2C6H5 | 7.3-6.9m(7H); 4.9-4.4m(3H); 4.2q(2H); 3.9-3.1m(5H); 3.0-2.4m(4H); 1.9-1.4m(2H); 1.2t(3H); 1.0t(3H) |
| 327 | 1 | H | CH(CH3)2 | H | CH2CH2C6H5 | 7.3-6.9m(7H); 4.9-4.4m(3H); 3.9-3.1m(4H); 3.0-2.4m(4H); 1.9-1.4m(2H); 1.0d(6H) |
| 328 | 1 | H | CH(CH3)2 | C2H5 | CH2CH2C6H5 | 7.3-6.9m(7H); 4.9-4.4m(3H); 4.2q(2H); 3.9-3.1m(4H); 3.0-2.4m(4H); 1.9-1.4m(2H); 1.2t(3H); 1.0d(6H) |
| 329 | 1 | H | CH2—CH=CH2 | H | CH2CH2C6H5 | 7.3-6.9m(7H); 5.8m(1H); 5.0-4.2m(5H); 3.9-3.1m(3H); 3.0-2.4m(4H); 1.9-1.4m(2H) |
| 330 | 1 | H | CH2—C≡CH | H | CH2CH2C6H5 | 7.3-6.9m(7H); 5.0-4.2m(5H); 3.9-3.1m(3H); 3.0-2.4m(4H); 1.9-1.4m(2H) |

| No. | | | | | | | | NMR |
|---|---|---|---|---|---|---|---|---|
| 331 | 1 | H | H | " | H | ⌗ (cyclobutyl) | H | CH₂CH₂C₆H₅ | 7.3-6.9m(7H); 4.8-4.3m(3H); 3.9-3.1m(4H); 3.0-2.4m(4H); 1.9-1.2m(8H) |
| 332 | 1 | H | H | (thiophene with ethyl substituents) | H | CH₃ | H | CH₂CH₂C₆H₅ | 7.3-6.9m(7H); 4.9-4.4m(3H); 3.9-3.0m(3H); 3.0-2.4m(4H); 2.3s(3H); 1.9-1.4m(2H) |
| 333 | 1 | H | H | " | H | C₂H₅ | H | CH₂CH₂C₆H₅ | 7.3-6.9m(7H); 4.9-4.4m(3H); 3.9-3.1m(5H); 3.0-2.4m(4H); 1.9-1.4m(2H); 1.0t(3H) |
| 334 | 1 | H | C₂H₅ | " | H | CH₃ | H | CH₂CH₂C₆H₅ | 7.3-6.9m(7H); 4.9-4.4m(3H); 4.2q(2H); 3.0-2.4m(4H); 2.3s(3H); 1.9-1.4m(2H); 1.2t(3H) |
| 335 | 1 | H | C₂H₅ | " | H | C₂H₅ | H | CH₂CH₂C₆H₅ | 7.3-6.9m(7H); 4.9-4.4m(3H); 4.2q(2H); 3.9-3.1m(5H); 3.0-2.4m(4H); 1.9-1.4m(2H); 1.2t(3H); 1.0t(3H) |
| 336 | 1 | H | H | " | H | CH(CH₃)₂ | H | CH₂CH₂C₆H₅ | 7.3-6.9m(7H); 4.9-4.4m(3H); 3.9-3.1m(4H); 3.0-2.4m(4H); 1.9-1.4m(2H); 1.0d(6H) |
| 337 | 1 | H | C₂H₅ | " | H | CH(CH₃)₂ | H | CH₂CH₂C₆H₅ | 7.3-6.9m(7H); 4.9-4.4m(3H); 4.2q(2H); 3.0-2.4m(4H); 1.9-1.4m(2H); 1.2t(3H); 1.0d(6H) |
| 338 | 1 | H | H | " | H | CH₂—CH=CH₂ | H | CH₂CH₂C₆H₅ | 7.3-6.9m(7H); 5.8m(1H); 5.0-4.2m(7H); 3.9-3.1m(3H); 3.0-2.4m(4H); 1.9-1.4m(2H) |
| 339 | 1 | H | H | " | H | CH₂—C≡CH | H | CH₂CH₂C₆H₅ | 7.3-6.9m(7H); 5.0-4.2m(5H); 3.9-3.1m(4H); 3.0-2.4m(4H); 1.9-1.4m(3H) |
| 340 | 1 | H | H | " | H | (cyclopentyl) | H | CH₂CH₂C₆H₅ | 7.3-6.9m(7H); 4.8-4.3m(3H); 3.9-3.1m(4H); 3.0-2.4m(4H); 1.9-1.4m(10H) |
| 341 | 1 | H | H | (thiophene with ethyl substituents) | H | CH₃ | H | CH₂CH₂C₆H₅ | 7.2s(7H); 4.8-4.4m(3H); 3.9-3.1m(3H); 3.0-2.4m(4H); 2.3s(3H); 1.9-1.4m(2H) |
| 342 | 1 | H | C₂H₅ | " | H | CH₃ | H | CH₂CH₂C₆H₅ | 7.2s(7H); 4.8-4.3m(3H); 4.2q(2H); 3.9-3.1m(5H); 3.0-2.4m(4H); 1.9-1.4m(2H); 1.0t(3H) |
| 343 | 1 | H | H | " | H | C₂H₅ | H | CH₂CH₂C₆H₅ | 7.2s(7H); 4.8-4.3m(3H); 3.9-3.1m(3H); 3.0-2.4m(4H); 1.9-1.4m(2H); 1.0t(3H) |
| 344 | 1 | H | C₂H₅ | " | H | C₂H₅ | H | CH₂CH₂C₆H₅ | 7.2s(7H); 4.8-4.3m(3H); 4.2q(2H); 3.9-3.1m(5H); 3.0-2.4m(4H); 1.9-1.4m(2H); 1.2t(3H); 1.0t(3H) |
| 345 | 1 | H | H | " | H | CH(CH₃)₂ | H | CH₂CH₂C₆H₅ | 7.2s(7H); 4.8-4.4m(3H); 3.9-3.1m(4H); 3.0-2.4m(4H); 1.9-1.4m(2H); 1.0d(6H) |
| 346 | 1 | H | C₂H₅ | " | H | CH(CH₃)₂ | H | CH₂CH₂C₆H₅ | 7.2s(7H); 4.8-4.4m(3H); 4.2q(2H); 3.1m(4H); 3.0-2.4m(4H); 1.9-1.4m(2H); ... |

-continued

| | | | | | |
|---|---|---|---|---|---|
| 347 | H | " | H | n-C₃H₇ | 1.3(3H); 1.0d(6H) |
| 348 | H | CH₂—CH(OCH₃)—CH₂ | H | CH₂CH₂C₆H₅ | 7.2s(7H); 4.8-4.3m(3H); 3.9-3.1m(5H); 3.0-2.4m(4H); 1.9-1.4m(4H); 1.05t(3H) |
| 349 | H | CH₂—CH(OCH₃)—CH₂ | H | CH₃ | 4.8-4.3m(1H); 2.2s(3H); 1.9-1.3m(2H) 2.3t(2H); 2.2s(3H); 3.6-3.0m+s(7H); 1.9-1.4m(3H); 1.2t(3H) |
| 350 | H | CH₂—CH(OCH₃)—CH₂ | C₂H₅ | CH₃ | 4.8-4.3m(1H); 4.2q(2H); 3.6-3.0m+s(7H); 2.3t(2H); 1.9-1.4m(2H); 1.2t(3H) |
| 351 | H | CH₂—CH(OCH₃)—CH₂ | H | CH(CH₃)₂ | 4.8-4.3m(1H); 3.8-3.0m+s(9H); 2.3t(2H); 1.9-1.4m(2H); 1.2t(3H) |
| 352 | H | CH₂—CH(OCH₃)—CH₂ | C₂H₅ | C₂H₅ | 4.8-4.3m(1H); 3.8-2.9m+s(10H); 1.9-1.4m(2H); 1.03d(9H) |
| 353 | H | CH₂—CH=CH | H | C₂H₅ | 4.8-4.3m(1H); 4.2q(2H); 3.8-2.9m+s(11H); 1.9-1.4m(2H); 1.2t(3H) 1.0d+t(6H) |
| 354 | H | CH₂—CH=CH | H | CH₂—CH=CH₂ | 6.4-5.5m(3H); 4.3-3.1m(6H); 2.3t (2H); 1.0t(3H) |
| 355 | H | CH₂—CH=CH | H | C₂H₅ | 6.4-5.5m(4H); 4.9-3.1m(10H); 4.2q(2H); 2.3t(2H); 1.2t(3H) |
| 356 | H | CH(CH₃)—CH₂—CH₂ | H | CH₃ | 6.5-5.5m(3H); 4.3-3.0m(7H); 1.0d+t(6H) |
| 357 | H | CH(CH₃)—CH₂—CH₂ | C₂H₅ | C₂H₅ | 4.8-4.2m(1H); 3.6-2.9m(4H); 2.4s (3H); 2.3t(2H); 1.9-1.4m(3H); 1.0d(3H) |
| 358 | H | CH(CH₃)—CH₂—CH₂ | H | CH₂CH₂CH₃ | 4.8-4.3m(1H); 4.2q(2H); 3.8-3.0m(6H); 2.3t (2H); 2.3t(2H); 1.9-1.4m(3H); 0.95d+t(6H) |
| 359 | H | CH(CH₃)—CH₂—CH₂ | C₂H₅ | CH₂—C≡CH | 4.8-4.3m(1H); 1.2t(3H); 1.0d(3H) |
| 360 | H | CH₂CH(C₆H₅)—CH₂ | H | CH₃ | 4.8-4.3m(1H); 3.8-2.9m(7H); 1.9-1.4m(5H); 1.0t+2d(9H) |
| 361 | H | CH₂CH(C₆H₅)—CH₂ | H | C₂H₅ | 4.8-4.0m(5H); 3.8-2.9m(5H); 1.9-1.4m(4H); 1.02d(6H) |
| 362 | 1 | CH(C₆H₅)—CH₂—CH₂ | H | C₂H₅ | 7.3-6.9m(5H); 4.8-4.3m(1H); 3.6-2.9m(5H); 2.3t(2H); 2.2s(3H); 1.9-1.4m(2H) |
| 363 | 1 | CH(C₆H₅)—CH₂—CH₂ | H | CH(CH₃)₂ | 7.3-6.9m(5H); 4.8-4.3m(1H); 3.6-2.8m(8H); 1.9-1.4m(2H); 1.05d(3H) |
| 364 | 1 | CH(C₆H₅)—CH₂—CH₂ | H | CH₃ | 7.3-6.9m(5H); 4.8-4.3m(1H); 3.8-2.9m(2H); 2.3t(2H) 1.9-1.4m(2H); 1.0t(2H) |
| | | | | | 7.3-6.9m(7H); 4.8-4.3m(1H); 3.8-2.9m(6H); 2.3t(2H)1.9-1.4m(2H); 1.0d(6H) |
| | | | | | 7.3-6.9m(5H); 4.8-4.3m(1H); 3.7-2.8m(7H); 1.9-1.3m(8H); 1.0d(3H) |
| 365 | 1 | (CH₂)₄ | C₂H₅ | CH₃ | 4.8-4.3m(1H); 3.6-2.8m(4H); 4.2q(2H); 2.4s (3H); 2.3t(2H); 1.9-1.4m(6H); 1.2t(3H) |
| 366 | 1 | (CH₂)₄ | H | CH₃ | 4.8-4.3m(1H); 3.6-2.8m(5H); 2.4s (3H); 1.9-1.4m(6H); 1.1d(3H) |
| 367 | 1 | (CH₂)₄ | H | C₂H₅ | 4.8-4.3m(1H); 3.6-2.8m(6H); 2.3t (2H); 1.9-1.4m(6H); 1.1t(3H) |
| 368 | 1 | (CH₂)₄ | H | CH(CH₃)₂ | 4.8-4.3m(1H); 3.8-2.8m(6H); 1.9-1.4m(7H); 1.0d(9H) |
| 369 | 1 | (CH₂)₄ | C₂H₅ | CH—C≡CH | 4.8-4.2m(3H); 3.8-2.9m(4H); 4.2q (2H); 2.3t(2H); 1.9-1.4m(7H); 1.2t(3H) |
| 370 | 1 | (CH₂)₄ | H | C₄H₉ | 4.8-4.3m(1H); 3.8-2.9m(7H); 1.9-1.4m(10H); 1.0d+t(6H) |

| | | | | | | -continued | |
|---|---|---|---|---|---|---|---|
| 377 | 1 | H | H | (CH₂)₅ | CH₃ | H | 4.8-4.3m(1H); 3.6-2.8m(4H); 2.4s(3H); 2.3t(2H); 1.9-1.4m(8H) |
| 378 | 1 | H | C₂H₅ | (CH₂)₅ | CH₃ | H | 4.8-4.0m(1H); 3.6-2.8m(4H); 2.4s(3H); 2.3t(2H); 1.9-1.4m(8H); 1.2t(3H) |
| 379 | 1 | H | H | (CH₂)₅ | C₂H₅ | H | 4.8-4.3m(1H); 3.8-2.8m(6H); 2.3t(2H); 1.9-1.4m(8H); 1.0t(3H) |
| 380 | 1 | H | C₂H₅ | (CH₂)₅ | C₂H₅ | H | 4.8-4.3m(1H); 4.2q(2H); 3.8-2.8m(6H); 2.3t(2H); 1.9-1.4m(8H); 1.2t(3H); 1.0t(3H) |
| 381 | 1 | H | H | (CH₂)₅ | CH(CH₃)₂ | CH₃ | 4.8-4.3m(1H); 3.8-2.8m(6H); 1.9-1.4m(8H); 1.03d (9H) |
| 382 | 1 | H | H | (CH₂)₅ | CH₂—CH=CH₂ | CH₃ | 5.8m(1H); 5.0-4.1m(5H); 3.8-2.9m(5H); 1.9-1.4m(8H); 1.0d(3H) |
| 383 | 1 | H | C₂H₅ | (CH₂)₅ |  | CH₃ | 4.7-4.3m(1H); 4.2q(2H); 3.7-3.0m(6H); 1.9-1.4m(8H); 1.0-1.5d+m(7H); 1.2t(3H) |
| 384 | 1 | H | H | (CH₂)₅ | n-C₄H₉ | H | 4.7-4.3m(1H); 3.9-3.0m(6H); 2.3t(2H); 1.9-1.4m(12H); 1.0t(3H) |
| 385 | 1 | H | H | CH₃O—⟨phenyl⟩ | CH₃ | H | 7.1-6.6m(3H); 4.8-4.3m(3H); 3.9s(3H); 3.8-3.0m(2H); 2.9-2.4m(4H) 2.3s(3H) |
| 386 | 1 | H | C₂H₄ | " | C₂H₅ | H | 7.1-6.6m(3H); 4.8-4.3m(3H); 4.2q(2H); 3.9s(3H); 3.8-3.0m(4H); 2.9-2.4m (4H); 1.2t(3H); 1.0t(4H) |
| 387 | 1 | H | H | " | C₂H₅ | H | 7.1-6.6m(3H); 4.8-4.3m(3H); 3.9s(3H); 3.8-3.0m(5H); 2.9-2.4m(2H); 1.0d+t(6H) |
| 388 | 1 | H | C₂H₅ | " | CH(CH₃)₂ | H | 7.1-6.6m(3H); 4.8-4.3m(3H); 3.9s(3H); 3.9-3.1m(4H); 4.2q(2H); 2.9-2.4m(2H); 1.2t(3H); 1.0d(9H) |
| 389 | 1 | H | H | " | CH₂—CH=CH₂ | CH₃ | 7.1-6.6m(3H); 5.8m(1H); 5.0-4.3(5H); 3.9s(3H); 3.8-2.9m(3H); 2.8-2.4m(2H); 1.05d(3H) |
| 390 | 1 | H | H | 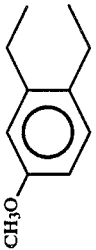 | CH₃ | H | 4.7-4.3m(1H); 3.6-2.9m(4H); 2.3t(2H); 2.2s(3H); 1.9-1.4m(12H) |
| 391 | 1 | H | H | " | C₂H₅ | H | 4.7-4.3m(1H); 3.8-2.9m(6H); 2.3t (2H); 1.9-1.4m(12H); 1.1t(3H) |
| 392 | 1 | H | C₂H₅ | " | C₂H₅ | H | 4.7-4.3m(1H); 4.2q(2H); 3.8-2.9m(6H); 2.3t(2H); 1.9-1.4m(12H); 1.3t(3H); 1.1t(3H) |
| 393 | 1 | H | H | " | CH(CH₃)₂ | H | 4.7-4.3m(1H); 4.0-3.1m(5H); 2.3t (2H); 1.9-1.4m(12H); 1.0d(6H) |
| 394 | 1 | H | H | " | CH₂—CH=CH₂ | CH₃ | 5.8q(1H); 5.0-4.1m(5H); 3.8-2.9 m(3H); 1.9-1.4m(12H); 1.0d(3H) |

| | | | | | -continued | |
|---|---|---|---|---|---|---|
| 395 | 1 | H | H | " | H | 4.7–4.3m(1H); 3.9–2.9m(5H); 2.3t(2H); 1.9–1.4m(18H) |
| 396 | 1 | H | H | (cyclobutyl) | H | 7.2–6.6m(4H); 4.9t(1H); 3.8–3.1m(2H); 2.9–2.2m(4H); 2.3s(3H) |
| 397 | 1 | H | H | $C_2H_5$ | H | 7.2–6.6m(4H); 4.9t(1H); 3.8–3.1m(4H); 2.9–2.2m(4H); 1.1t(3H) |
| 398 | 1 | H | H | $C_2H_5$ | $CH_3$ | 7.2–6.6m(4H); 4.9t(1H); 3.8–2.8m(3H); 2.9–2.2m(2H); 1.0t+d(6H) |
| 399 | 1 | H | H | $CH(CH_3)_2$ | H | 7.2–6.6m(4H); 4.9t(1H); 3.9–2.9m(3H); 2.9–2.2m(4H); 1.0d(6H) |

| | n | R¹ | R¹' | R²–R³ | R⁴ | R⁵ | R⁶ | |
|---|---|---|---|---|---|---|---|---|
| 400 | 1 | H | H | " | CH₂—C≡CH | H | H | 7.2–6.6m(4H); 4.9t(1H); 4.3–3.2m (4H); 2.9–2.2m(4H); 1.8s(1H) |
| 401 | 1 | H | H | " | CH₂—CH=CH₂ | H | CH₃ | 7.2–6.6m(4H); 5.8m(1H); 5.0–4.2m (5H); 3.9–2.9m(3H); 1.0d(3H) |
| 402 | 1 | H | H | CH₃O–[cyclohexyl with two ethyl substituents] | CH₃ | H | H | 4.8–4.3m(1H); 3.8–2.9m + s(8H); 2.3t(2H); 2.2s(3H); 1.9–1.4m(10H) |
| 403 | 1 | H | H | " | C₂H₅ | H | H | 4.8–4.3m(1H); 3.8–2.9m + s(10H); 2.3t(2H); 1.9–1.4m(10H); 1.0t(3H) |
| 404 | 1 | H | H | " | C₂H₅ | H | CH₃ | 4.8–4.3m(1H); 3.8–2.8m + s(11H); 1.9–1.4m(10H); 1.0d + t(6H) |
| 405 | 1 | H | H | " | CH(CH₃)₂ | H | H | 4.8–4.3m(1H); 3.8–2.9m + s(9H); 2.3t(2H); 1.9–1.4m(10H); 1.0d(6H) |
| 406 | 1 | H | H | " | [cyclobutyl] | H | CH₃ | 4.8–4.3m(1H); 3.8–2.9m + s(10H); 1.9–1.4m(16H); 1.0d(6H) |
| 407 | 1 | H | H | [cyclohexyl with ethyl and methyl substituents] | CH₃ | H | H | 4.9–4.4m(1H); 4.0–3.1m(3H); 2.3t (2H); 2.2s(3H); 1.9–1.4m(11H) |
| 408 | 1 | H | H | " | C₂H₅ | H | H | 4.9–4.4m(1H); 4.0–3.1m(5H); 2.3t (2H); 1.9–1.4m(11H) 1.1t(3H) |
| 409 | 1 | H | H | " | CH(CH₃)₂ | H | H | 4.9–4.4m(1H); 4.0–3.1m(4H); 2.3t (2H); 1.9–1.4m(11H); 1.0d(6H) |
| 410 | 1 | H | H | " | C₂H₅ | H | CH₃ | 4.9–4.4m(1H); 4.0–3.0m(7H); 1.9–1.4m(11H); 1.0d + t(6H) |
| 411 | 1 | H | H | " | CH₂—CH=CH₂ | H | CH₃ | 5.8m(1H); 5.1–4.3m(5H); 4.0–3.2m (4H); 1.9–1.4m(11H); 1.0d(3H) |
| 412 | 1 | H | H | CH₃O–[cyclohexyl with ethyl and methyl substituents] | CH₃ | H | H | 4.9–4.4m(1H); 4.0–3.1m + s(7H); 2.4s (3H); 2.3t(2H); 1.9–1.4m(9H) |

-continued

| No. | | | | | | | NMR |
|---|---|---|---|---|---|---|---|
| 429 | 1 | H | H | " | C₂H₅ | H | CH₃ | 3.9–3.1m(4H); 2.3t(2H); 2.9–2.4m(2H); 7.3–6.9m(2H); 4.9–4.3m(3H); 3.9–3.0m(5H); 2.9–2.4m(2H); 1.1t + d(6H) |
| 430 | 1 | H | H | " | CH(CH₃)₂ | H | H | 7.3–6.9m(2H); 4.8–4.4m(3H); 3.8–3.0m(3H); 2.9–2.4m(2H); 2.3t(2H); 1.0d(6H) |
| 431 | 1 | H | H | " | CH(CH₃)₂ | H | CH₃ | 7.3–6.9m(2H); 4.9–4.4m(3H); 3.9–3.1m(4H); 2.9–2.4m(2H); 1.0d(9H) |
| 432 | 1 | H | H | [3,4-diethylthiophene] | C₂H₅ | H | H | 7.2s(2H); 4.9–4.4m(3H); 3.9–3.1m(4H); 2.3t(2H); 2.9–2.4m(2H); 1.0t(3H) |
| 433 | 1 | H | H | " | C₂H₅ | H | CH₃ | 7.2s(2H); 4.9–4.4m(3H); 3.9–3.0m(5H); 2.9–2.4m(2H); 1.1t + d(6H) |
| 434 | 1 | H | H | " | CH(CH₃)₂ | H | H | 7.2s(2H); 4.9–4.4m(3H); 3.9–3.2m(3H); 2.9–2.4m(2H); 2.3t(2H); 1.0d(6H) |
| 435 | 1 | H | H | " | CH(CH₃)₂ | H | CH₃ | 7.2s(2H); 4.9–4.4m(3H); 3.9–3.1m(4H); 2.9–2.4m(2H); 1.1d(9H) |
| 436 | 1 | H | H | [thiophene] | CH₃ | H | H | 4.8–4.2m(3H); 3.6–3.0m(2H); 2.7–2.2m(4H); 2.4s(3H) |
| 437 | 1 | H | C₂H₅ | " | CH₃ | H | H | 4.8–4.2m(5H); 3.6–3.0m(2H); 2.7–2.2m(4H); 2.4s(3H); 1.2t(3H) |
| 438 | 1 | H | H | " | C₂H₅ | H | CH₃ | 4.8–4.2m(3H); 3.7–3.0m(5H); 2.7–2.4m(2H); 1.0t + d(6H) |
| 439 | 1 | H | C₂H₅ | " | CH(CH₃)₂ | H | H | 4.8–4.4m(3H); 4.2m(2H); 3.9–3.0m(4H); 2.7–2.4m(2H); 1.0d(9H); 1.2t(3H) |
| 440 | 1 | H | H | " | CH₃ | H | CH₂CH₂C₆H₅ | 7.2s(5H); 4.8–4.2m(3H); 3.9–3.0m(3H); 2.9–2.2m(4H); 1.9–1.4m(2H); 2.3s(3H) |
| 441 | 1 | H | C₂H₅ | " | C₂H₅ | H | CH₂CH₂C₆H₅ | 7.2s(5H); 4.8–4.3m(3H); 4.2q(2H); 3.9–3.0m(5H); 2.9–2.2m(4H); 1.9–1.4m(2H); 1.2t(3H); 1.0t(3H) |
| 442 | 1 | H | H | " | CH₂CH=CH₂ | H | CH₂CH₂C₆H₄—4-F | 7.4–6.9m(4H); 5.8m(1H); 5.1–4.2(5H); 3.9–3.0m(3H); 2.9–2.2m(4H); 1.9–1.4m(2H) |
| 443 | 1 | H | C₂H₅ | " | CH₂—C≡CH | H | CH₂CH₂C₆H₄—4-OCH₃ | 6.9–6.3m(4H); 4.8–4.0m(5H); 3.9–3.1m(3H); 3.9s(3H); 2.9–2.2m(4H); 1.9–1.4m(2H) |

-continued

| | | | | | | |
|---|---|---|---|---|---|---|
| 444 | 1 | H | " | 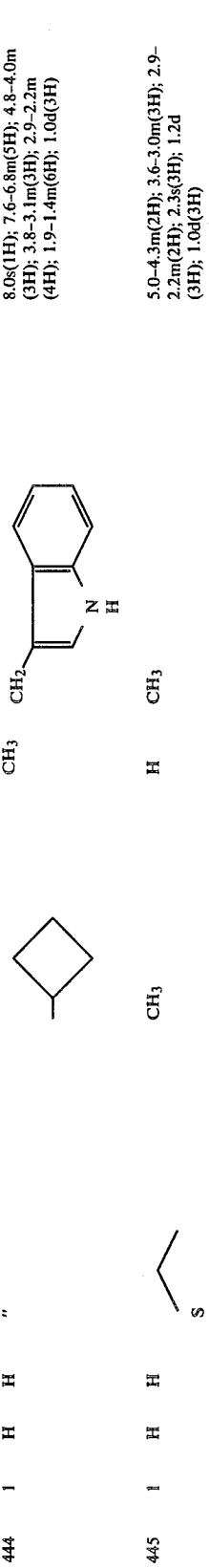 | CH₃ | (4H); 1.9–1.4m(3H); 1.2t(3H); 4.2q(2H) 8.0s(1H); 7.6–6.8m(5H); 4.8–4.0m (3H); 3.8–3.1m(3H); 2.9–2.2m (4H); 1.9–1.4m(6H); 1.0d(3H) |
| 445 | 1 | H | H | 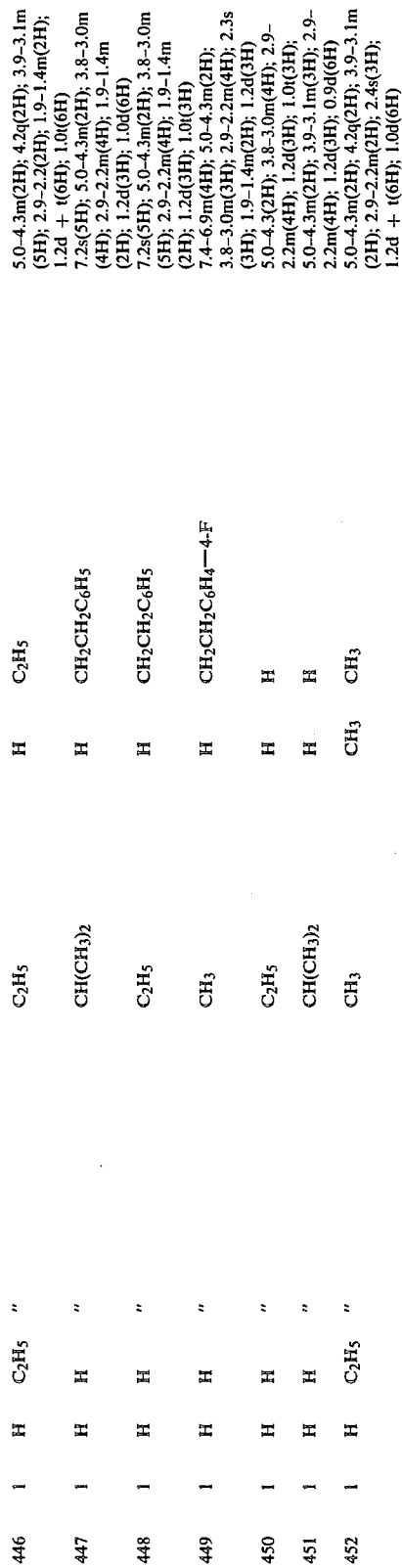 | CH₃ | 5.0–4.3m(2H); 3.6–3.0m(3H); 2.9–2.2m(2H); 2.3s(3H); 1.2d (3H); 1.0d(3H) |
| 446 | 1 | H | C₂H₅ | CH₃ | C₂H₅ | 5.0–4.3m(2H); 4.2q(2H); 3.9–3.1m (5H); 2.9–2.2m(2H); 1.9–1.4m(2H); 1.2d + t(6H); 1.0t(6H) |
| 447 | 1 | H | H | CH(CH₃)₂ | CH₂CH₂C₆H₅ | 7.2s(5H); 5.0–4.3m(2H); 3.8–3.0m (4H); 2.9–2.2m(4H); 1.9–1.4m (2H); 1.2d(3H); 1.0d(6H) |
| 448 | 1 | H | H | C₂H₅ | CH₂CH₂C₆H₅ | 7.2s(5H); 5.0–4.3m(2H); 3.8–3.0m (5H); 2.9–2.2m(4H); 1.9–1.4m (2H); 1.2d(3H); 1.0t(3H) |
| 449 | 1 | H | H | CH₃ | CH₂CH₂C₆H₄—4-F | 7.4–6.9m(4H); 5.0–4.3m(2H); 3.8–3.0m(3H); 2.9–2.2m(4H); 2.3s (3H); 1.9–1.4m(2H); 1.2d(3H) |
| 450 | 1 | H | H | C₂H₅ | H | 5.0–4.3(2H); 3.8–3.0m(4H); 2.9–2.2m(4H); 1.2d(3H); 1.0t(3H) |
| 451 | 1 | H | H | CH(CH₃)₂ | H | 5.0–4.3m(2H); 3.9–3.1m(3H); 2.9–2.2m(4H); 1.2d(3H); 0.9d(6H) |
| 452 | 1 | H | C₂H₅ | CH₃ | CH₃ | 5.0–4.3m(2H); 4.2q(2H); 3.9–3.1m (2H); 2.9–2.2m(2H); 2.4s(3H); 1.2d + t(6H); 1.0d(6H) |
| 453 | 1 | H | H | 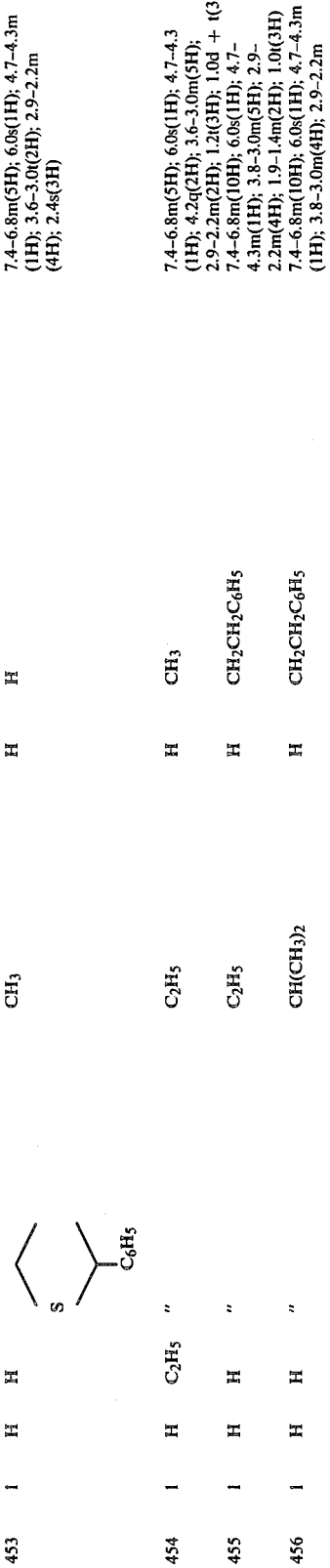 | H | 7.4–6.8m(5H); 6.0s(1H); 4.7–4.3m (1H); 3.6–3.0m(2H); 2.9–2.2m (4H); 2.4s(3H) |
| 454 | 1 | H | H | C₂H₅ | CH₃ | 7.4–6.8m(5H); 6.0s(1H); 4.7–4.3 (1H); 4.2q(2H); 3.6–3.0m(5H); 2.9–2.2m(2H); 1.2t(3H); 1.0d + t(3H) |
| 455 | 1 | H | H | C₂H₅ | CH₂CH₂C₆H₅ | 7.4–6.8m(10H); 6.0s(1H); 4.7–4.3m(1H); 3.8–3.0m(5H); 2.9–2.2m(4H); 1.9–1.4m(2H); 1.0t(3H) |
| 456 | 1 | H | H | CH(CH₃)₂ | CH₂CH₂C₆H₅ | 7.4–6.8m(10H); 6.0s(1H); 4.7–4.3m (1H); 3.8–3.0m(4H); 2.9–2.2m |

-continued

| No. | | | | | | | NMR |
|---|---|---|---|---|---|---|---|
| 457 | 1 | H | C₂H₅ | " | H | CH₃ | CH₂CH₂C₆H₄—4-F | (4H); 1.9-1.4m(2H); 1.0d(6H) 7.5-6.8m(9H); 6.0s(1H); 4.7-4.3m (1H); 4.2q(2H); 3.8-3.0m(3H); 2.9-2.2m(4H); 2.3s(3H); 1.9-1.4 m(2H); 1.2t(3H) |
| 458 | 1 | H | H | " | H | CH₂CH₂CH₃ | CH₂CH₂—C₆H₄—2-CH₃ | 7.5-6.9m(9H); 6.0s(1H); 4.7-4.3m (1H); 3.8-3.0m(5H); 2.9-2.2m (4H); 2.1s(3H); 1.9-1.4m(4H); 1.0t(3H) |
| 459 | 1 | H | C₂H₅ | " | H |  | CH₂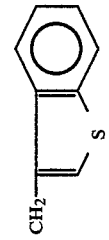 | 7.5-6.9m(10H); 6.0m(1H); 4.7-4.3m (1H); 3.8-3.0m(4H); 4.2q(2H); 2.9-2.2m(4H); 1.2t(3H); 1.0-0.5m(4H) |
| 460 | 1 | H | H | 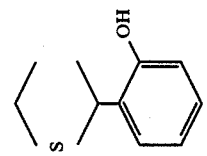 | H | CH₃ | H | 7.1-6.4m(4H); 6.0s(1H); 4.7-4.3m(1H); 3.6-3.0t(2H); 2.9-2.2m(4H); 2.4s(3H) |
| 461 | 1 | H | C₂H₅ | " | H | CH₃ | H | 7.1-6.4m(4H); 6.0s(1H); 4.7-4.3m(1H); 4.2q(2H); 3.6-3.0t (2H); 2.9-2.2m(4H); 2.4s(3H); 1.2t(3H) |
| 462 | 1 | H | H | " | H | C₂H₅ | CH₂CH₂C₆H₅ | 7.3-6.4m(9H); 6.0s(1H); 4.7-4.3m (1H); 3.8-3.0m(5H); 2.9-2.2m (4H); 1.9-1.4m(2H); 1.0t(3H) |
| 463 | 1 | H | C₂H₅ | " | H | CH₃ | CH₂CH₂C₆H₅ | 7.3-6.4m(9H); 6.0s(1H); 4.7-4.3m (1H); 4.2q(2H); 3.8-3.0m(3H); 1.9-2.2m(4H); 1.9-1.4m(2H); 2.2 s(3H); 1.2t(3H) |
| 464 | 1 | H | H | " | H | CH(CH₃)₂ | CH₂CH₂C₆H₅ | 7.3-6.4m(9H); 6.0s(1H); 4.7-4.3m (1H); 3.8-2.9m(4H); 2.9-2.2m (4H); 1.9-1.4m(2H); 1.0d(6H) |
| 465 | 1 | H | H | " | H | CH₂—CH=CH₂ | CH₂CH₂C₆H₄—4-F | 7.3-6.4m(8H); 6.0-5.6m(2H); 5.0-4.1m(5H); 3.6-3.1m(3H); 2.9-2.2m(4H); 1.9-1.4m(2H) |
| 466 | 1 | H | C₂H₅ | " | H | CH₂CH₂CH₃ | CH₂CH₂—C₆H₄—4-OCH₃ | 7.1-6.3m(8H); 6.0s(1H); 4.7-4.3m (1H); 4.2q(2H); 3.9s(3H); 3.8-3.0m(5H); 2.9-2.2m(4H); 1.9-1.4m(2H); 1.2t(3H); 1.0t(3H) |
| 467 | 1 | H | H | " | H | C₂H₅ | C₂H₅ | 7.1-6.5m(4H); 6.0s(1H); 4.7-4.3m (1H); 3.8-3.0m(5H); 2.9-2.4m (2H); 1.9-1.4m(2H); 1.0t(6H) |
| 468 | 1 | H | H | " | H | C₂H₅ | n-C₄H₉ | 7.1-6.5m(4H); 6.0s(1H); 4.7-4.3m (1H); 3.8-3.0m(5H); 2.9-2.4m (2H); 1.9-1.4m(6H); 1.0t(6H) |

-continued
| | | | | | | |
|---|---|---|---|---|---|---|
| 469 | 1 | H | C₂H₅ | —CH₂CH₂—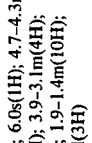 | H | 7.3–6.5m(7H); 6.0s(1H); 4.7–4.3m(1H); 3.8–3.0m(5H); 2.9–2.4m(4H); 1.9–1.4m(2H); 1.0t(3H) |
| 470 | 1 | H | C₂H₅ | —CH₂CH₂—C₆H₃—2,6-Cl₂ | H | 7.4–6.5m(7H); 6.0s(1H); 4.7–4.3m(1H); 3.8–3.0m(5H); 2.9–2.4m(4H); 1.9–1.4m(2H); 1.0t(3H) |
| 471 | 1 | H | 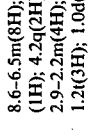 | —CH₂CH₂— | CH₃ | 8.6–6.5m(8H); 6.0s(1H); 4.7–4.3m(1H); 4.2q(2H); 3.9–3.1m(4H); 2.9–2.2m(4H); 1.9–1.4m(10H); 1.2t(3H); 1.0d(3H) |
| 472 | 1 | H | CH₃ | | H | 7.1–6.5m(4H); 6.0s(1H); 4.7–4.3m(1H); 3.6–3.1m(3H); 2.9–2.4m(2H); 2.3s(3H); 1.0d(3H) |
| 473 | 1 | H | CH₃ | C₂H₅ | CH₃ | 7.1–6.5m(4H); 6.0s(1H); 4.7–4.3m(1H); 4.2q(2H); 3.6–3.1m(3H); 2.9–2.4m(2H); 2.3s(3H); 1.0d(3H) |
| 474 | 1 | H | C₂H₅ | 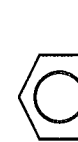 | H | 13.4s(1H); 7.7s(1H); 4.9–4.3m(3H); 4.2q(2H); 3.9–3.1m(4H); 2.9–2.5m(2H); 2.3t(2H); 1.2t(3H); 1.0t(3H) |
| 475 | 1 | H | C₂H₅ | 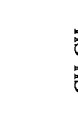 | H | 7.3–6.9m(2H); 4.9–4.4m(3H); 4.2q(2H); 3.9–3.1m(4H); 2.3t(2H); 2.9–2.4m(2H); 1.2t(3H);1.0t(3H) |
| 476 | 1 | H | C₂H₅ |  | H | 7.3–6.9m(2H); 4.8–4.4m(3H); 4.2q(2H); 3.9–3.1m(4H); 2.9–2.5m(2H); 2.3t(2H); 1.2t(3H); 1.0t(3H) |
| 477 | 1 | H | CH₃ |  | H | 4.7–4.3m(1H); 4.2q(2H); 3.6–2.9m(4H); 2.3t(2H); 2.2s(3H); 1.9–1.4m(12H); 1.1t(3H) |
| 478 | 1 | H | C₂H₅ | ″ | CH₃ | 4.7–4.3m(1H); 4.2q(2H); 3.8–2.9m(7H); 1.9–1.4m(12H); 1.2t(3H); 1.1d + t(6H) |
| 479 | 1 | H | CH(CH₃)₂ | ″ | H | 4.7–4.3m(1H); 4.2q(2H); 4.0–3.1m(5H); 2.3t(2H); 1.9–1.4m(12H); |

-continued

| | | | | | |
|---|---|---|---|---|---|
| 480 | H | C₂H₅ | " | CH₃ | H | 1.2t(3H); 1.0d(6H) 4.7-4.3m(1H); 4.2q(2H); 3.8-2.9m (5H); 2.2s(3H); 1.9-1.4m(12H); 1.2t(3H); 1.1d(3H) |
| 481 | H | C₂H₅ | (2-ethyl-methylphenyl) | CH₃ | H | 7.2-6.6m(4H); 4.9t(1H); 4.2q (2H); 3.8-3.1m(2H); 2.9-2.2m(4H) 2.3s(3H); 1.2t(3H) |
| 482 | H | C₂H₅ | " | C₂H₅ | H | 7.2-6.6m(4H); 4.9t(1H); 4.2q (2H); 3.9-2.9m(3H); 2.9-2.2m (4H); 1.2t(3H); 1.0d(6H) |
| 483 | H | C₂H₅ | " | CH(CH₃)₂ | H | 7.2-6.6m(4H); 4.9t(1H); 4.2q (2H); 3.8-3.1m(2H); 2.9-2.3m(3H) 2.3s(3H); 1.2t(3H); 1.0d(3H) |
| 484 | H | C₂H₅ | " | CH₃ | CH₃ | |
| 485 | H | C₂H₅ | (CH₃O-cyclohexyl diethyl) | CH₃ | H | 4.8-4.3m(1H); 4.2q(2H); 3.8-2.9m + s(8H); 2.3s(3H); 2.2t(2H); 1.9-1.4m(10H); 1.2t(3H) |
| 486 | H | C₂H₅ | " | C₂H₅ | H | 4.8-4.3m(1H); 4.2q(2H); 3.8-2.9m + s(10H); 2.2t(2H); 1.9-1.4m(10H); 1.2t(3H); 1.0t(3H) |
| 487 | H | C₂H₅ | " | CH(CH₃)₂ | H | 4.8-4.3m(1H); 4.2q(2H); 3.9-2.9m + s(9H); 2.2t(2H); 1.9-1.4m (10H); 1.2t(3H); 0.9d(6H) |
| 488 | H | C₂H₅ | " | CH₃ | CH₃ | 4.8-4.3m(1H); 4.2q(2H); 3.9-2.9m + s(9H); 2.3s(3H); 1.9-1.4m (10H); 1.2t(3H); 1.0d(3H) |
| 489 | H | C₂H₅ | (cyclohexyl diethyl) | CH₃ | H | 4.9-4.4m(1H); 4.2q(2H); 4.0-3.1m (3H); 2.3t(2H); 2.2s(3H); 1.9-1.4m(11H); 1.2t(3H); 1.0t(3H) |
| 490 | H | C₂H₅ | " | C₂H₅ | H | 4.9-4.4m(1H); 4.2q(2H); 4.0-3.1m (5H); 2.3t(2H); 1.9-1.4m(11H); 1.2t(3H); 1.0t(3H) |
| 491 | H | C₂H₅ | " | CH(CH₃)₂ | H | 4.9-4.4m(1H); 4.2q(2H); 4.0-3.1m (4H); 2.3t(2H); 1.9-1.4m(11H); 1.2t(3H); 1.05d(6H) |
| 492 | H | C₂H₅ | " | CH₃ | CH₃ | 4.9-4.4m(1H); 4.2q(2H); 4.0-3.0m (4H); 2.2s(3H); 1.9-1.4m(11H); 1.2t(3H); 1.0d(3H) |

-continued

| | | | | | | | |
|---|---|---|---|---|---|---|---|
| 493 | 1 | H | C₂H₅ | CH₃O-[cyclohexyl(ethyl)(methyl)] | CH₃ | H | 4.9–4.4m(1H); 4.2q(2H); 4.0–3.1m + s(7H); 2.4s(3H); 2.3t(2H); 1.9–1.4m(9H); 1.2t(3H) |
| 494 | 1 | H | C₂H₅ | " | C₂H₅ | H | 4.9–4.4m(1H); 4.2q(2H); 4.0–3.1m + s(9H); 2.3t(2H); 1.9–1.4m(9H); 1.2t(3H); 1.0t(3H) |
| 495 | 1 | H | C₂H₅ | " | CH(CH₃)₂ | H | 4.9–4.4m(1H); 4.2q(2H); 4.0–3.1m + s(8H); 2.3t(2H); 1.9–1.4(9H) 1.2t(3H); 0.9d(6H) |
| 496 | 1 | H | C₂H₅ | " | CH₃ | CH₃ | 4.9–4.4m(1H); 4.2q(2H); 4.0–2.9m + s(8H); 2.3s(3H); 1.9–1.4m(9H); 1.2t(3H); 1.0d(3H) |

We claim:
1. A compound of the formula I

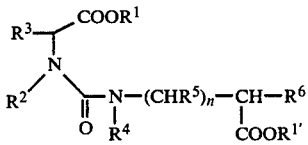

in which
n is a whole number between 0 and 3 inclusive;
$R^1$ and $R^{1'}$, being the same or different, are hydrogen; alkyl or alkenyl having 1-8 C atoms; phenyl or benzyl, each unsubstituted or monosubstituted by methyl, halogen, methoxy or nitro;
$R^2$ and $R^3$ together with the C and N atoms carrying them form a 2-azabicyclo[3.3.0]octane ring system, which is unsubstituted, monosubstituted or distubstituted by hydroxyl, alkoxy having 1-3 C atoms, alkyl having 1-3 C atoms or phenyl;
$R^4$ is hydrogen; alkyl, alkenyl, alkadienyl, alkynyl, alkeninyl or alkadiynyl having 1-8 C atoms; cycloalkyl having 3-6 C atoms; phenyl, benzyl, phenethyl or phenylpropyl, each of which is unsubstituted, monosubstituted or disubstituted by halogen, hydroxyl, acetoxy, carboxy, carboxamido, sulfonamido, nitro, methyl ethyl, methoxy, ethoxy or methylenedioxy;
$R^5$ is hydrogen; alkyl having 1-5 C atoms; hydroxyl or alkoxy having 1-3 C atoms;
$R^6$ is hydrogen; alkyl having 1-12 C atoms; cycloalkyl having 3-12 C atoms; alkenyl having 2-12 C atoms; phenyl or naphthyl, each of which is unsubstituted, monosubstituted or disubstituted by halogen, hydroxyl, acetoxy, carboxy, carboxamido, sulfonamido, nitro, methyl, ethyl, methoxy, ethoxy or methylenedioxy; alkyl having 1-6 C atoms, which is monosubstituted by halogen, hydroxyl, alkoxy having 1-3 C atoms, phenoxy, amino, dialkylamino having 1-6 C atoms, alkanoylamino having 1-3 C atoms, mercapto, alkylthio having 1-3 C atoms, phenylthio, phenylsulfinyl, phenylsulfonyl, phenyl biphenylyl, or naphthyl, the phenyl or naphthyl each being unsubstituted, monosubstituted or disubstituted by halogen, methyl, ethyl, methoxy, ethoxy, nitro, amino, methylamino, dimethylamino, acetylamino, cyano, methylenedioxy or sulfonamido; heteroaryl selected from the group consisting of pyridyl, thienyl, indolyl, benzothienyl, imidazolyl, pyrazolyl and thiazolyl, said heteroaryl being unsubstituted mono-substituted or disubstituted by halogen, methyl, ethyl, methoxy, ethoxy, nitro, amino, methylamino dimethylamino, acetylamino, cyano, methylenedioxy, sulfonamido or phenyl; or physiologically tolerable salts thereof.

2. The compound as claimed in claim 1, wherein n is a whole number from 0 to 2, inclusive,
$R^1$ and $R^{1'}$ are hydrogen, alkyl or alkenyl having 1 to 4 C atoms, or benzyl unsubtituted or substituted in the phenyl nucleus by methyl, halogen, methoxy or nitro;
$R^4$ is hydrogen, straight-chain or branched alkyl, alkenyl or alkinyl having 1 to 5 C atoms, cycloalkyl having 3 to 6 C atoms, phenyl, benzyl or phenethyl;
$R^5$ is hydrogen, methyl, ethyl, hydroxyl, methoxy or benzyl;
$R^6$ is hydrogen, alkyl having 1 to 8 C atoms or phenyl which can be monosubstituted or disubstituted by methyl, halogen, methoxy, acetoxy or nitro; or alkyl with 1-4 C atoms substituted by halogen, hydroxyl, methoxy, ethoxy, phenoxy, amino, methylamino, dimethylamino, anilino, acetylamino, benzamido, mercapto, phenylthio, phenylsulfinyl, phenylsulfonyl; phenyl, which is unsubstituted, monosubstituted or disubstituted by halogen, methyl, ethyl, methoxy, ethoxy, nitro, amino, methylamino, dimethylamino, acetylamino, cyano, methylenedioxy or sulfonamido, biphenylyl; or heteroaryl which is unsubstitued or substituted by halogen, methyl, methoxy and phenyl.

3. The compound as claimed in claim 1, wherein n is 0 or 1,
$R^1$ and $R^{1'}$ are hydrogen, methyl ethyl, n-butyl, t-butyl, benzyl or p-nitrophenyl,
$R^4$ is methyl, ethyl, n-propyl, n-butyl, isopropyl, isobutyl, cyclopropyl, cyclobutyl, allyl, butenyl, propargyl, butinyl or tert.-butyl;
$R^5$ is hydrogen, methyl or benzyl;
$R^6$ is hydrogen, straight-chain or branched alkyl or alkenyl having 1 to 6 C atoms or cycloalkyl having 3 to 6 C atoms; or alkyl having 1 to 3 C atoms which is substituted by phenoxy, ethoxy, methoxy, dimethylamino, anilino, benzamido, phenylthio, phenylsulfinyl, phenylsulfonyl; phenyl which is unsubstituted, monosubstituted or disubstituted by halogen, methyl, methoxy, nitro, amino, methylamino, dimethylamino, acetylamino, cyano or methylenedioxy, biphenylyl; or heteroaryl which is optionally substituted by chlorine, methyl, methoxy or phenyl.

4. The compound as claimed in claim 2, wherein the carbon atom which carries the substituent $R^3$ has the S-configuration.

5. The compound as claimed in claim 3, wherein the carbon atom which carried the substituent $R^3$ has the S-configuration.

6. The compound as claimed in claim 1, wherein n is 1, $R^1$ is hydrogen,
$R^4$ is ethyl, $R^5$ is hydrogen, $R^6$ is β-phenylethyl and the carbon atom which carries the substituent $R^3$ has the S-configuration.

7. The compound as claimed in claim 1, wherein n is 1, $R^1$ is hydrogen, $R^2$ and $R^3$, together with the C and N atoms carrying them, are the 2-azabicyclo[3.3.0]octane system, $R^4$ is ethyl, $R^5$ is hydrogen and $R^6$ denotes β-phenylethyl.

8. Hypotensive composition containing a hypotensively effective concentration of a compound defined in claim 1 and a carrier therefor.

9. Hypotensive dosage unit containing from about 20 mg. to about 3 g. of a compound defined in claim 1.

10. Hypotensive dosage unit containing from about 50 mg. to about 1 g. of a compound defined in claim 1.

11. A method of treatment which comprises administering to a patient suffering from hypertension a hypotensively effective amount of a compound defined in claim 1.

12. The compound as claimed in claim 1 which is [N-Ethyl-N-(4-phenyl-2-carboethoxybutyl)-carbamoyl]-cis-endo-2-azabicyclo[3.3.0]octane-3-carboxylic acid.

13. A compound of the formula I as claimed in claim 1 which is [N-Ethyl-N-(4-phenyl-2-carboxybutyl)-carbamoyl]-cis-endo-2-azabicyclo[3.3.0]octane-3-carboxylic acid.

* * * * *